(12) United States Patent
Meruelo et al.

(10) Patent No.: US 7,910,093 B2
(45) Date of Patent: Mar. 22, 2011

(54) METHOD FOR DETECTING CANCER CELLS AND MONITORING CANCER THERAPY

(75) Inventors: Daniel Meruelo, Scarborough, NY (US); Jen-Chieh Tseng, Woodside, NY (US)

(73) Assignee: New York University, New York, NY (US)

(*) Notice: Subject to any disclaimer, the term of this patent is extended or adjusted under 35 U.S.C. 154(b) by 382 days.

(21) Appl. No.: 10/920,030

(22) Filed: Aug. 16, 2004

(65) Prior Publication Data

US 2005/0152838 A1 Jul. 14, 2005

Related U.S. Application Data

(60) Provisional application No. 60/496,486, filed on Aug. 19, 2003.

(51) Int. Cl.
*A01N 63/00* (2006.01)
*A61K 48/00* (2006.01)
*C12Q 1/68* (2006.01)

(52) U.S. Cl. .................... 424/93.2; 424/93.6; 435/6

(58) Field of Classification Search .................. 424/93.2
See application file for complete search history.

(56) References Cited

U.S. PATENT DOCUMENTS

| | | |
|---|---|---|
| 5,091,309 A | 2/1992 | Schlesinger et al. |
| 5,217,879 A | 6/1993 | Huang et al. |
| 5,739,026 A | 4/1998 | Garoff |
| 5,789,245 A | 8/1998 | Dubensky, Jr. et al. |
| 5,814,482 A | 9/1998 | Dubensky, Jr. et al. |
| 5,843,723 A | 12/1998 | Dubensky, Jr. et al. |
| 6,015,686 A | 1/2000 | Dubensky, Jr. et al. |
| 6,015,694 A | 1/2000 | Dubensky, Jr. et al. |
| 6,190,666 B1 | 2/2001 | Garoff et al. |
| 6,224,879 B1 | 5/2001 | Sjoberg |
| 6,242,259 B1 | 6/2001 | Polo et al. |
| 6,329,201 B1 | 12/2001 | Polo et al. |
| 6,342,372 B1 | 1/2002 | Dubensky, Jr. et al. |
| 6,376,236 B1 | 4/2002 | Dubensky, Jr. et al. |
| 6,391,632 B1 | 5/2002 | Dubensky, Jr. et al. |
| 6,426,196 B1 | 7/2002 | Dubensky, Jr. et al. |
| 6,451,592 B1 | 9/2002 | Dubensky, Jr. et al. |
| 6,458,560 B1 | 10/2002 | Dubensky, Jr. et al. |
| 6,465,634 B1 | 10/2002 | Dubensky, Jr. et al. |
| 6,566,093 B1 | 5/2003 | Liljestrom et al. |
| 6,592,874 B2 | 7/2003 | Schlesinger et al. |
| 6,692,750 B1 | 2/2004 | Sjoberg et al. |
| 6,730,297 B1 | 5/2004 | Davidson et al. |
| 6,770,283 B1 | 8/2004 | Garoff et al. |
| 2005/0031594 A1 | 2/2005 | Shino |

FOREIGN PATENT DOCUMENTS

| | | |
|---|---|---|
| WO | 99/18226 | 4/1999 |
| WO | 99/44423 | 9/1999 |
| WO | 00/62735 | 10/2000 |
| WO | WO 02/76468 | * 3/2002 |
| WO | 02/074920 | 9/2002 |

OTHER PUBLICATIONS

Hay (Trends in Biotechnology, 2004. vol. 22, No. 10, pp. 501-503).*
Loimas et al. (2001, Cancer Gene Therapy, vol. 8, No. 2, pp. 137-144).*
Tseng et al., "In Vivo Antitumor Activity of Sindbis Viral Vectors," Journal of the National Cancer Institute, Dec. 2002, vol. 94, No. 23. pages 1790-1802.
Ying H. et al., Cancer Therapy Using a Self-Replicating RNA Vaccine, Nature Medicine, Jul. 1999, pp. 823-827, vol. 5, No. 7, Nature Publishing Group, New York, USA.
Schlesinger S. et al., "Alphavirus Vectors for Gene Expression and Vaccines", Current Opinion in Biotechnology, Oct. 1999, pp. 434-439, vol. 10, No. 5, London, GB.
Perri, Slyvia et al. "Replicon Vectors Derived from Sindbis Virus and Semliki Forest Virus That Establish Persistent Replication in Hest Cells." Journal of Virology, Oct. 2000, pp. 9802-9807, vol. 74, No. 20.
Leitner, Wolfgang W. et al. "Enhancement of Tumor-specific Immune Response With Plasmid DNA Replicon Vectors." Cancer Research, Jan. 1, 2000, pp. 51-55.
Hariharan, Mangala J. et al. "DNA Immunization Againstr Herpes Simplex Virus: Enhanced Efficacy Using a Sindbis Virus-Based Vector." Journal of Virology, Feb. 1998, pp. 950-958, vol. 72, No. 2.
Gardner, Jason P. et al. "Infection of Human Dendritic Cells by a Sindbis Virus Replicon Vector Is Determined by a Single Amino Acid Substitution in the E2 Glycoprotein." Journal of Virology, Dec. 2000, pp. 11849-11857, vol. 74, No. 24.
Polo, John M. et al. "Stable Alphavirus Packaging Cell Lines for Sindbis Virus- and Semliki Forest Virus-Derived Vectors." Proc. Natl. Acad. Sci. USA, Apr. 1999, pp. 4598-4603, vol. 96.
Dubensky, Thomas W., Jr. et al. "Sindbis Virus DNA-Basd Expression Vectors: Utility for In Vitro and In Vivo Gene Transfer." Journal of Virology, Jan. 1996, pp. 508-519, vol. 70, No. 1.
Xiong, Cheng et al. "Sindbis Virus: An Efficient, Broad Host Range Vector for Gene Expression in Animal Cells." Science, Mar. 3, 1989, pp. 1188-1191, vol. 243.
Levis, Robin et al. "Engineered Defecctive Interfering RNAs of Sindbis Virus Express Bacterial Chloramphenicol Acetyltransferase in Avian Cells." Porc. Natl. Acad. Sci. USA, Jul. 1987, pp. 4811-4815, vol. 84.
Murphy A-M et al. "Inhibition of Human Lung Carcinoma Cell Growth by Apoptosis Using Semliki Forest Virus Recombinant Particles." Gene Therapy, 2000, p. 1477-82, vol. 7.
Asselin-Paturel C. et al. "Transfer of the Murine IL-12 Gene in Vivo by a Semiliki Forest Virus Vector Induces B16 Tumor Regression Through Inhibition of Tumor Blood Vessel Formation Monitered by Doppler Ultrasonography" Gene Therapy, 1998, p. 615, vol. 5.

(Continued)

*Primary Examiner* — Valarie Bertoglio
(74) *Attorney, Agent, or Firm* — Fish & Richardson P.C.

(57) ABSTRACT

Disclosed herein are methods for identifying cancer cells and monitoring anti-cancer therapy in the body of a mammal by systemically delivering Sindbis viral vectors. The vector can specifically target and identify tumor cells in mice growing subcutaneously, intraperitoneally, intrapancreatically, or in the lungs. These findings demonstrate the remarkable specificity of the Sindbis vector system that is relatively safe and can specifically target tumor cells throughout the body via the bloodstream.

12 Claims, 23 Drawing Sheets

OTHER PUBLICATIONS

Klimp et al. "Activation of Peritoneal Cells Upon in Vivo Transfection with a Recumbinant Alphavirus Expressing GM-CSF." Gene Therapy, Feb. 2000, p. 300-7, vol. 8, No. 4.

Li et al. "Rescue of Sindbis Virus-Specific RNA Replication and Transcription by using Vaccinia Virus Recombinant." J. of Virology, Dec. 1991, p. 6714-23, vol. 65, No. 12.

Cheng et al. "Cancer Immunotherapy using Sindbis Virus Replicon Particles Encoding VP22-Antigen Fusion." Human Gene Therapy, Mar. 1, 2002, p. 553-68, vol. 13, No. 4.

Velders at al. "Eradication of Established Tumors by Vaccination with Venezuelan Equine Encephalitis Virus Replicon Particles Delivering Human Papilomavirus 16 E7 RNA." Cancer Research, Nov. 1, 2001, p. 7861-67, vol. 61, No. 21.

Smerdou et al. "Two-Helper System for Production of Recombinant Semliki Forest Virus Particles." Journal of Virology, vol. 73, No. 2, Feb. 1999, pp. 1092-1098.

Zhang, et al. "Cloning of Human IL-12 p40 and p35 DNA into the Semliki Forest Virus Vector: Expression of IL-12 in Human Tumor Cells." Gene Therapy, 1997, pp. 367-374.

Miller, et al. "Targeted Vectors for Gene Therapy." The FASEB Journal, vol. 9, Feb. 1995, pp. 190-199.

Deonarain, "Ligand-Targeted Receiptor-Mediated Vectors for Gene Delivery." Exp. Opin: Ther. Patents, vol. 8, No. 1, 1998, pp. 53-69.

Verma, et al. "Gene Therapy—Promises, Problems and Prospects." Nature, vol. 389, Sep. 18, 1997, pp. 239-242.

Crystal, "Transfer of Genes to Humans: Early Lessons and Obstacles to Success." Science, vol. 270, Oct. 20, 1995, pp. 404-410.

Pouton, et al. "Key Issues in Non-Viral Gene Delivery." Advanced Drug Delivery Reviews, 2001, pp. 187-203.

Read, et al. "Barriers to Gene Delivery Using Synthetic Vectors." Advances in Genetics, vol. 53, 2005, pp. 19-46.

Higashikawa, et al. "Kinetic Analyses of Stability of Simple and Complex Retorviral Vectors." Virology 280, 2001, pp. 124-131.

DePolo, et al. "The Resistance of Retroviral Vectors Produced from Human Cells to Serum Inactivation In Vivo and In Vitro Is Primate Species Development." Journal of Virology, Aug. 1999, pp. 6708-6714.

Alemany, et al. "Blood Clearance Rates of Adenovirus Type 5 in Mice." Journal of General Virology, 2000, pp. 2605-2609.

Sung, et al. "TNFa and IFNg Induced by Innate Anti-Adenoviral Immune Responses Inhibit Adenovirus-Mediated Transgene Expression." Molecular Therapy, vol. 3, No. 5, May 2001, pp. 757-767.

Unno, et al. "Oncolytic Viral Therapy for Cervical and Ovarian Cancer Cells by Sindbis Virus AR339 Strain." Clin. Cancer. Res., vol. 11, No. 12, Jun. 15, 2005, pp. 4553-4560.

Wang, et al., "High-Affinity Laminin Receptor Is a Receptor for Sindbis Virus in Mammalian Cells." Journal of Virology, vol. 66, No. 8, Aug. 1992, pp. 4992-5001.

Jan, et al., "Induction of Apoptosis by Sindbis Virus Occurs at Cell Entry and Does Not Require Virus Replication," Journal of Virology, vol. 73, No. 12, Dec. 1999, pp. 10296-10302.

Campo, et al. "Detection of Laminin Receptor mRNA in Human Cancer Cell Lines and Colorectal Tissues by In Situ Hybridization." American Journal of Pathology, vol. 141, No. 5, Nov. 1992, pp. 1073-1083.

Rice, et al, 2001. "In vivo imaging of light-emitting probes." Journal of Biomedical Optics 6(4): 432-440.

* cited by examiner

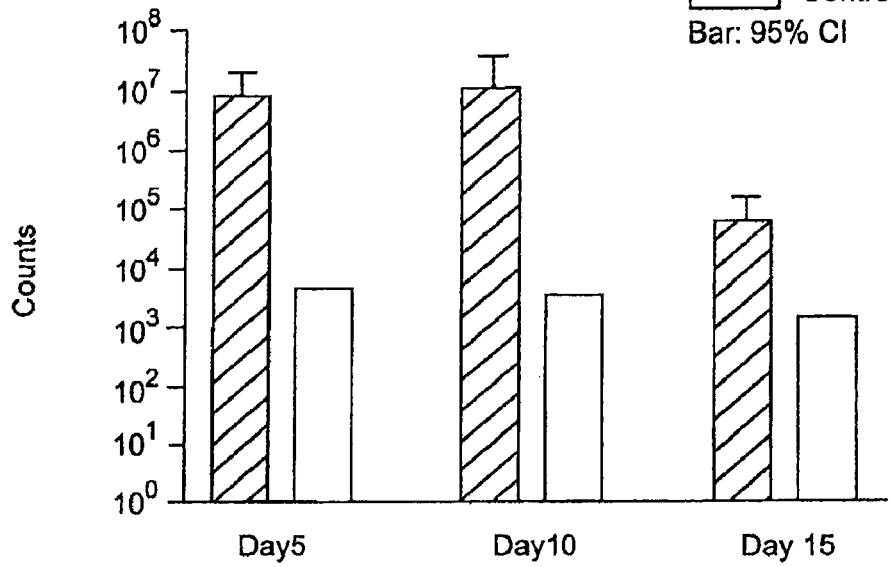
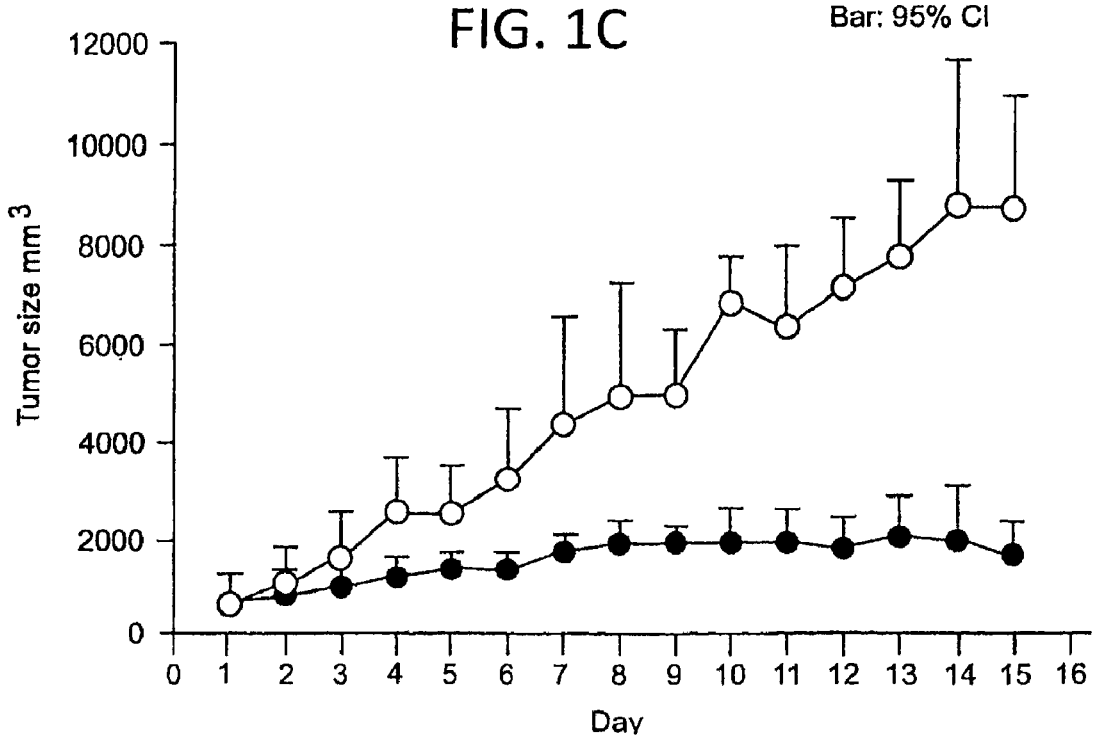

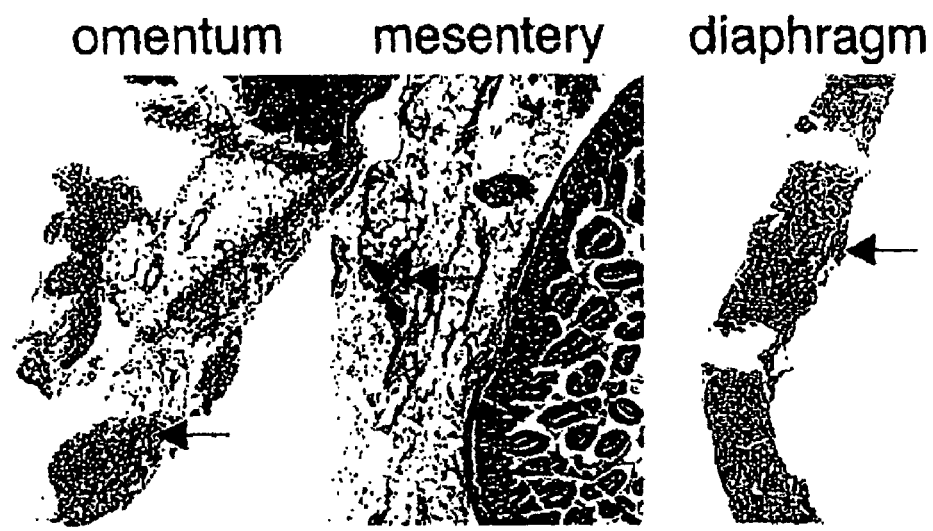
FIG. 4A
FIG. 4B
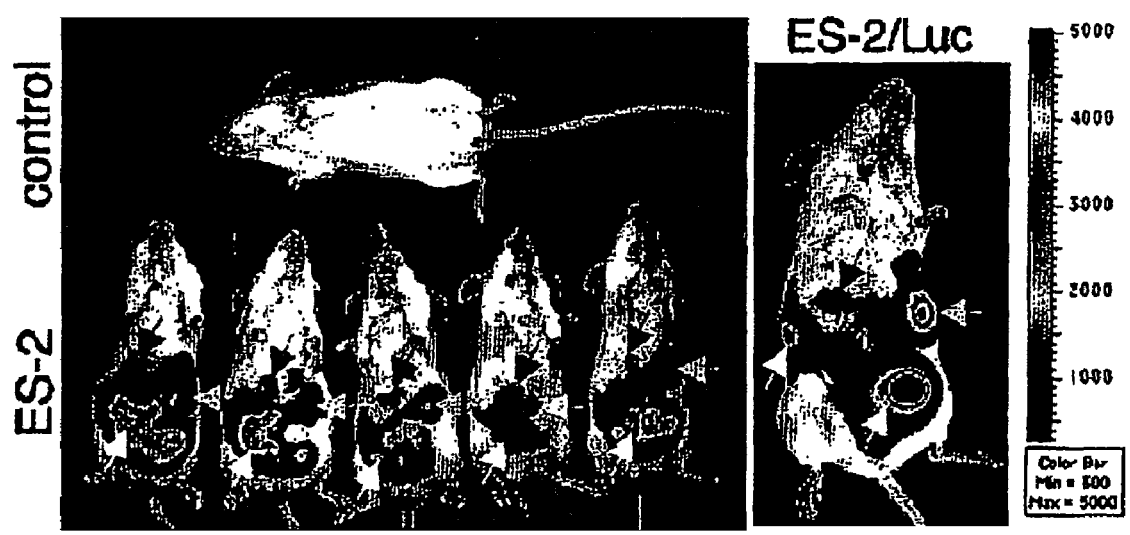

Overlay

Photograph

SEQUENCE LISTING

```
<160> NUMBER OF SEQ ID NOS: 5

<210> SEQ ID NO 1
<211> LENGTH: 19
<212> TYPE: RNA
<213> ORGANISM: Homo sapiens
```

```
<400> SEQUENCE: 1
ccagauccag gcagccuuc                                                    19

<210> SEQ ID NO 2
<211> LENGTH: 22
<212> TYPE: DNA
<213> ORGANISM: artificial
<220> FEATURE:
<223> OTHER INFORMATION: primer

<400> SEQUENCE: 2
ctcaagagga cctgggagaa gc                                                22

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
tggcagcagc aaacttcagc                                                   20

<210> SEQ ID NO 4
<211> LENGTH: 26
<212> TYPE: DNA
<213> ORGANISM: artificial
<220> FEATURE:
<223> OTHER INFORMATION: primer

<400> SEQUENCE: 4
caccagggct gcttttaact ctggta                                            26

<210> SEQ ID NO 5
<211> LENGTH: 24
<212> TYPE: DNA
<213> ORGANISM: artificial
<220> FEATURE:
<223> OTHER INFORMATION: primer

<400> SEQUENCE: 5
ccttgacggt gccatggaat tgc                                               24
```

METHOD FOR DETECTING CANCER CELLS AND MONITORING CANCER THERAPY

This application claims priority to U.S. Ser. No. 60/496,486, filed on Aug. 19, 2003. This prior application is incorporated herein by reference.

The United States Government has certain rights to this invention by virtue of funding received from Public Health Service Grants CA22247 and CA68498 from the National Cancer Institute, National Institutes of Health, Department of Health and Human Services and U.S. Army grant OC000111.

BACKGROUND OF THE INVENTION

The likelihood of successful cancer gene therapy would be greatly enhanced by availability of a vector that could be delivered systemically and would have specific anti-tumor targeting capability along with the ability to induce death in primary and metastatic tumor cells. Vectors based on a prototype alphavirus, Sindbis virus, which were originally developed for efficient in vitro gene transfer to mammalian cells[1], appear to have the desired properties[2]. Several factors contribute to the vectors' potential. First, in nature Sindbis virus is transmitted to mammals by mosquito bites[3]. After infection, the virus has a relatively long half-life in blood, and subsequently spreads to all organs of the body, including the brain[4,5]. Gene transfer vectors based on Sindbis virus retain the blood-borne attribute, which makes them suitable for systematic administration. Second, the surface receptor on mammalian cells for Sindbis infection has been identified as the 67-kDa high affinity laminin receptor (LAMR)[6,7]. LAMR has been found to be significantly upregulated in numerous human cancers[8-15]. Higher expression of LAMR has been related to the increasing invasiveness and malignancy of different cancers[16,17]. Also, in contrast to normal cells, the majority of the LAMR on cancer cells may not be occupied by laminin[18,19]. High levels of unoccupied LAMRs in tumor versus normal cells appear to confer on Sindbis viral vectors the ability to preferentially infect tumor cells. Third, Sindbis infection is highly apoptotic in mammalian cells[20-23]. Therefore the vectors themselves are sufficiently apoptotic to eliminate tumor cells that are infected.

Conventional monitoring cancer therapies include computed tomography (CT), magnetic resonance imaging (MRI) and positron-emission (PET). CT requires the use of x-rays and is not suitable for pregnant patients. MRI detects the subtle differences in physiological environments, such as blood-flood, between normal and tumor tissues. In order to enhance the sensitivity and specificity, MRI for monitoring cancer therapy requires the use of contrast agents which, however, do not specifically target tumor cells. In addition, both CT and MRI are unable to detect microscopic tumors in vivo. PET, which detects the emitted radioactivity within the body, is more sensitive for monitoring cancer therapy compared with CT and NI. Recent PET technologies take advantage of the increased glucose transfer and glycolide activities in tumor cells and use a radioactive glucose homologue, $^{18}$F-fluro-2-deoxyglucose (FDG), for PET imaging. FDG is metabolized and accumulated within cells with higher glocolytic activities and produce PET signals. However, since some normal cell types also have higher glycolytic activity, such as gray matter in brain, using PET for monitoring cancer therapy in these regions is not suitable.

Therefore, what is needed in the art is improved methods for detecting cancer cells in the body or a mammal and monitoring anti-cancer therapy which overcomes the deficiencies mentioned above.

SUMMARY OF THE INVENTION

Disclosed herein is the unexpected discovery that Sindbis viral vectors, whether systemically delivered by intraperitoneal (i.p.) or intravenous (i.v.) injection, target tumors growing subcutaneously (s.c.), intraperitoneally (i.p.), intrapancreatically or in the lungs of SCID mice.

In one aspect, the present invention provides a method for monitoring anti-cancer therapy in a mammal comprising administering to a mammal in need of such treatment a diagnostically effective amount of a Sindbis virus comprising a gene encoding a detectable label, and determining the amount of cancer cells in the body of said mammal, wherein the amount of cancer cells is proportional to the amount of label produced by said cancer cells.

In a further aspect, the present invention provides a method for identifying cancer cells in the body of a mammal comprising administering to a mammal in need of such treatment of diagnostically effective amount of a Sindbis virus comprising a gene encoding a detectable label and assaying for said label, wherein said cell is a cancer cell if it expresses said label.

In a still further embodiment, the present invention is directed to a method for determining the amount of cancer cells in the body of a mammal comprising the steps of (a) administering to a mammal in need of such treatment a diagnostically effective amount of a Sindbis virus comprising a gene encoding detectable label, and (b) determining the amount of said label, wherein the amount of a cancer cell in the body of said mammal is proportional to the amount of said label.

These and other aspects of the present invention will be apparent to those of ordinary skill in the art in light of the present description of claims and drawings.

Figure 1B:
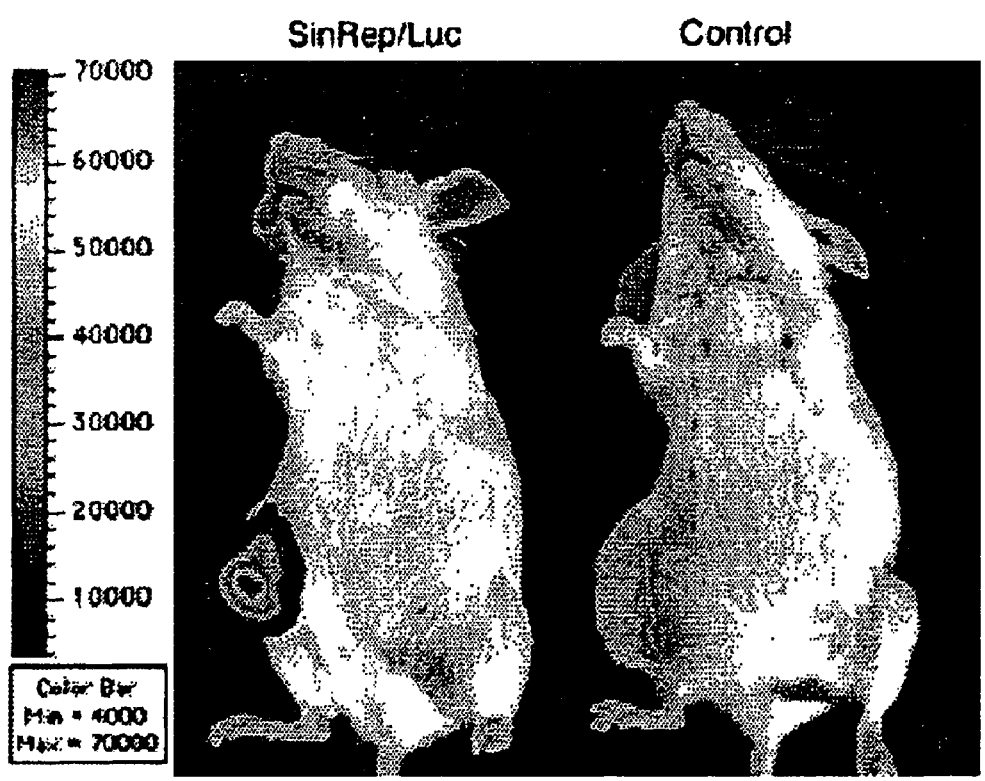
FIGS. 1(A-E) Intraperitoneal delivery of a Sindbis vector, SinRep/Luc, to SICD mice bearing s.c. BHK tumors results in tumor-specific infection and tumor growth suppression. The daily i.p. treatment started on day 1. a, On day 5 we observed tumor-specific bioluminescence signal as determined by total photon counts from tumor-covered areas (n=5). Control tumor-bearing mouse (n=1) received no vector treatment and showed no significant bioluminescence signal compared with treated mice. In treated mice the tumor-specific bioluminescence signals dropped significantly on day 15. Bar: 95% confidence intervals. b, On day 10, the SinRep/Luc vector treatment resulted in strong bioluminescence in treated BHK tumor, as determined by IVIS® imaging, and caused noticeable tumor growth inhibition compared with untreated control tumor. c, SinRep/Luc treatments significantly suppressed the BHK tumor growth as analyzed by two-way ANOVA (P<0.0001). Bar: 95% confidence intervals. d, I.p. SinRep/Luc treatment resulted in substantial size difference and extensive cell death in s.c. BHK tumors. BHK tumor cross-sections were obtained on day 15 from two control mice that received no SinRep/Luc treatment, and from two treated mice with hematoxylin and eosin. The hematoxiphilic regions (arrow #1) designate the viable tumor tissues while the eosinophilic areas (arrow # 2) indicate the necrotic tumor tissues. Bar: 10 mm. e, At higher magnification (20x), the control tumors showed less cell death and the boundary between viable and necrotic tissues is more irregular. In contrast, the SinRep/Luc-treated tumors showed extensive and homogeneous tumor death except for the very outer rim.

The β-galactosidase activities in infected cells were analyzed the day after infection. For each designed MOI three independent assays were performed and the data presented as the percentage of activities in infected ES-2/Fluc cells.

DETAILED DESCRIPTION OF THE INVENTION

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Monitoring cancer therapy" is defined herein as determining the relative amount of cancer cells in the body of a patient before, during or after anti-cancer therapy.

In vivo diagnostics refers to in vivo imaging methods, which permit the detection of a labeled molecule that is specifically produced by cancer cell in the subject's body. Such methods include magnetic resonance imaging (MRI), positron-emission tomography (PET) and single photon emission tomography (SPECT).

"Anti-cancer therapy" is defined herein as chemotherapy, radiation, immunotherapy, surgery, combinations thereof and the like as known by those of ordinary skill in the art.

The methods according to the present invention can be used to identify and monitor the therapy of all kinds of tumors and metastases. In a specific embodiment, the method according to the present invention is used to identify and monitor the therapy of solid tumors, non-limiting examples of which are hepatic carcinoma, melanoma, epidermoid carcinoma, pancreatic cancer, brain malignancies (such as neuroblastoma, glioblastoma, glioma, medulloblastoma, astrocytoma, acoustic neuroma, oligodendroglioma and meningioma), breast cancer, lung cancer (such as small cell lung and non-small cell lung cancer) ovarian adenocarcinoma, colon cancer, prostate cancer, bladder cancer, and renal cancer.

According to the invention, a therapeutic compound (i.e., Sindbis virus) can be formulated in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intraarteriole, intramuscular, intradermal, subcutaneous, intraperitoneal, intraventricular, and intracranial administration.

Pursuant to the present invention, an amount of the diagnostic compound of the present invention effective to label (infect) all of the cancer cells in a subject is administered. The diagnostically effective amounts to be administered are as follows: In one preferred embodiment the diagnostically effective amount of Sindbis vector to be administered to a mammal, would broadly range between about $10^9$ and about $10^{12}$ CFU per Kg body weight of the recipient and preferably between about $10^{10}$ and about $10^{11}$ CFU per Kg body weight of the recipient. This would translate to a human patient receiving broadly between about $10^{10}$ CFU and about $10^{12}$ CFU and preferably between about $10^{10}$ and about $10^{11}$ CFU. Since significant monitoring effects may be achieved using lower dosages, in another preferred embodiment the diagnostically effective amount of Sindbis vector to be administered would broadly range between about $10^6$ and about $10^9$ CFU per kg body weight of the recipient and preferably between about $10^7$ and about $10^8$ CFU per kg body weight of the recipient. The precise amounts will depend on the severity of the disease condition being monitored, other factors, such as diet modification that are implemented, the weight, age, and sex of the subject, and other criteria, which can be readily determined according to standard good medical practice by those of skill in the art.

The diagnostic agent of the present invention, i.e. Sindbis virus, is based on a blood-borne virus and therefore, intravenous administration is preferred for monitoring. However, for some special cancers, such as ovarian cancer that spread throughout the peritoneal cavity, intraperitoneal injection is preferred since the disease mostly concentrates there.

The present invention is based on the relationship between the receptor recognized by Sindbis virus and the role this molecule plays in cancer. The mammalian cellular receptor for Sindbis infection has been identified as the 67-kDa high affinity laminin receptor (LAMR)[16], a glycosylated membrane protein that mediates cellular interactions with the extracellular matrix. The expression of LAMR is up-regulated in several human cancers; higher levels provide cancer cells growth advantages such as greater propensity for invasiveness and metastasis[18,19]. Thus, pursuant to the present invention, LAMR serve as a "tumor specific" receptor for Sindbis vectors.

In one preferred embodiment, the present invention can be used as a diagnostic tool for identifying cancer cells in the body of a mammal. In this case, a subject is administered a diagnostically-effective amount (as set forth above) of a Sindbis vector comprising a detectable label, and assaying for cells containing the label. The Sindbis vector will only deliver the label to cells having High Affinity Laminin Receptors, i.e., cancer cells.

The present inventors have discovered that imaging can be translated into photon counts produced by the detectable label delivered to cancer cells and that these are proportional to the amount of tumor cells that remain alive. Therefore, the present invention can be used to monitor anti-cancer therapy as follows. Patients can be administered a diagnostically-effective amount of a Sindbis vector comprising a detectable label before the onset of treatment, and this value can be compared to one obtained upon administration of a diagnostically effective amount of a Sindbis virus comprising a detectable label after therapy has been completed. In this way, it is possible to determine the extent of tumor kill.

In another preferred embodiment, a patient is administered a diagnostically-effective amount of a Sindbis vector comprising a detectable label, and determining the amount of label produced. Since only living tumor cells would contain the label, therapy would continue only until a minimal amount of label is detected.

It had been previously shown that in vivo tumors were targeted by Sindbis vectors, primarily by means of a visual effect on tumor reduction and by immunohistochemistry that indicated that tumor killing was occurring. These studies are laborious and require animal sacrifice, plus it is not always possible to determine that vector had in fact hit all tumor cells and only tumor cells.

There are several surprising, unexpected results from practicing the invention:

(1) The sensitivity and ease of demonstration of tumor targeting that can be achieved by imaging transcends what was expected. Targeting with Sindbis vectors can image virtually all tumor cells and metastatic lesions. Normal cells are not targeted. It is this sensitivity that first suggested that Sindbis vectors could be used for diagnostic purpose, something that had not been previously considered.

(2) Further, imaging can be translated into photon counts and these are proportional to the amount of tumor cells that remain alive. Previously animals were treated with Sindbis vectors possibly beyond the point that it was necessary because, until the animals were sacrificed it was not possible to determine the extent of tumor kill. Thus, it was realized that imaging could reduce the duration of treatments because diminutions in the signal were indicative that tumor kill had taken place and the number of tumor cells that were alive had decreased.

(3) Imaging is better than pharmacodynamics, which can only estimate how long treatments must be done based on blood levels. Imaging is more comparable to tissue pharmacodynamics, which is generally very difficult to do. It is comparable to measuring the actual amount of drug in the tumor cells themselves in the live patient. Because the vector is self-amplifying, it turns out that imaging is much easier to do than tissue pharmacodynamics and requires no biopsies of tissues.

(4) Imaging with Sindbis vectors can be used to monitor treatments other than with Sindbis, because as tumor loads decrease, e.g., because of chemotherapy, less signals would occur from Sindbis vectors that appear capable of specifically targeting most tumor cells.

Since Sindbis viral vectors are gene transfer vectors, the cancer cells are labeled using genetic markers incorporated in the Sindbis virus. This is a unique concept of the present invention in that cell "labeling" is usually thought of as a cell surface phenomenon employing chemical conjugates of, e.g., antibodies. Pursuant to the present invention, cells are labeled internally. The genes useful for live tumor monitoring or labeling include but are not limited to the Herpes Simplex Virus thymidine kinase (HSV-tk) gene, [Iijima, Y., Ohno, K., K. Sawai, B. Levin, and D. Meruelo. Cell-specific targeting of a thymidine kinase ganciclovir gene therapy system using a recombinant Sindbis virus vector. International J. Cancer, 80: 110-118, 1999], the Green Fluorescence Protein (GFP) gene, [Cormack, B. P. et al. (1966) FACS-optimized mutants of the green fluorescent protein (GFP). *Gene* 173: 33-38] the Firefly luciferase (Fluc) gene, [de Wet, J. R., et al. (1987) Firefly luciferase gene: structure and expression in mammalian cells Mol. Cell Biol. 7 (2), 725-737], the *Renilla* luciferase (Rluc) gene [Lorenz, W. W. et al. (1991) Isolation and expression of a cDNA encoding *Renilla reinformis* luciferase, Proc. Natl. Acad. Sci. U.S.A. 88 (10), 4438-4442] and the dopamine-2 receptor ($D_2R$) gene. The use of the $D_2R$ gene as a reporter gene in living animals is disclosed in MacLaren et al. (Gene Therapy 6: 785-791 (1999)) and Yaghoubi et al. (Gene Therapy 8: 1072-1080 (2001)) These genes can be incorporated into Sindbis vectors using techniques well known to those of ordinary skill in the art, as described in Bredenbeek P. J. et al. (1993) (Sindbis virus expression vectors: packaging of RNA replicons by using defective helper RNAs, J. Virol.; 67(11): 6439-46.)

Sindbis vectors for use in the present invention are commercially available from Invitrogen (Carlsbad, Co). The vectors can be propagated and titered on BHK cells (available from American Type Collection (ATCC), Manassas, Va.).

Cells expressing the genetic markers of the present invention can be identified as follows: for the HSV-tk gene, the subject can be administered radiolabeled 9-[(4[$^{18}$F]fluro-3-hydroxymethylbutyl)guanine (FHBG), administered intravenously, about 6000 μCi/Kg body weight of the recipient, (commercially available from PET Imaging Science Center, U. of South California). Expression of HSV-tk activity in tumor cells results in the accumulation of radiolabeled FHBG and can be monitored by Positron Emission Tomography (PET). In vivo GFP expressing tumor cells can be monitored by fluoresence microscopic examination of tissue sections. Tissue sections of Fluc or Rluc expressing tumor cells can be monitored by Cooled Charge-Coupled Device (CCD) cameras in vivo (commercially available from Xenogen Corp., Alamenda, Calif.). $D_2R$ activity can be identified by administering 3-(2-[$^{18}$F]fluoroethyl)spiperone ([$^{18}$F]FESP) and monitored by PET.

A subject to whom the diagnostic compound of the present invention has been administered as an effective diagnostic monitor for a disease or disorder is preferably a human, but can be any animal, including a laboratory animal in the context of a clinical trial or screening or activity experiment. Thus, as can be readily appreciated by those of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

When formulated in a pharmaceutical composition, the diagnostic compound of the present invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage form carrier, including but not limited to one or more of a binder (for compressed pills), an encapsulating agent, a flavorant, and a colorant. Suitable pharmaceutical carriers are described in "Remington's Pharmaceutical Sciences" by E. W. Martin.

Sindbis virus is a blood-borne virus. Therefore, gene therapy vectors based on this virus have an advantage over other viral vectors that are not adapted to travel in the bloodstream. This property is largely responsible for the observation that systemic administration of Sindbis viral vectors by i.p. or i.v. injections, target and infect tumors growing s.c. (FIG. 1), i.p. (FIG. 3), intrapancreatically (FIG. 4), or in the lungs (FIG. 5). Thus, the blood-borne nature of Sindbis viral vectors provides them the capacity to monitor cancer therapy.

Replication competent Sindbis virus infects skin, connective tissues and muscle[4]. In addition, it also causes encephalitis in young mice[26]. However, the infection is sub-clinical and not virulent in adult mice. A neuroadapted Sindbis virus strain inoculated in the peripheral tissue in 11-day-old weanling mice shows local replication and spread to central nervous system (CNS) via the bloodstream. The present invention uses replication-defective Sindbis vectors derived from a wild-type virus (strain AR339) that has not been specifically neuroadapted. Probably for this reason, substantial bioluminescence signals from CNS or other normal tissues, except for low-level signals at the site(s) of injection after several vector treatments was not observed. There was also no evidence of adverse effects following injection of the vectors of the present invention. All mice appeared healthy during the experiments, excepting for tumor growth and the associated symptomology.

With proper reporter genes, as shown herein, Sindbis vectors are useful for systemic detection of metastasized tumors. This potential of Sindbis vectors was exemplified in a mouse model of advanced ovarian cancer (FIG. 4b), which, as the cases in the human counterpart, show tumor dissemination and widespread metastases throughout the peritoneal cavity.

As shown below, advanced ovarian cancer can be induced in SCID mice by i.p. injection of ES-2 human ovarian carcinoma cells. Microscopic metastastized ES-2 tumors were readily detected throughout the intraperitoneal cavity 5 days after a 2×10$^6$ ES-2 cell i.p. injection (FIG. 4a). In addition to tumoral ascites formation, the tumors grow aggressively within the peritoneal cavity and metastasize further to liver, lung, kidney and, in some cases to the brain. Without treatment, mice developed severe liver failure that is probably responsible for the high and rapid mortality seen.

For patients, in addition to systemic chemotherapy, surgery is the usual treatment for this disease. However, complete tumor removal is technically impossible, especially for the most advanced cases. Therefore, the goal of surgical management are accurate diagnosis and optimal cytoreducton. In this application the ability of Sindbis vector to detect microscopic metastasized tumors at an early stage in animals with advanced ovarian cancer was demonstrated.

The present invention is described below in working examples which are intended to further describe the invention without limiting the scope therein.

In Examples 1-5 below, the following materials and methods were used.

Cells and Vector Preparation

Baby hamster kidney (BHK) and BHKSINLuc2 cells were obtained from the American Type Culture Collection (ATCC, Manassas, Va.) and maintained in minimum essential alpha-modified media (αMEM, JRH Bioscience, Lenexa, Kans.) supplemented with 5% fetal bovine serum (FBS) 100 μg/mL of penicillin-streptomycin (Mediatech, Inc., Hemdon, Va.) and 0.5 μg/mL of amphotericin B (Mediatech, Inc.). The BHKSINLuc cells are derived from BHK cells and are stably transfected with a plasmid carrying a defective luciferase replicon under the control of a Rous sarcoma virus promoter[24].

SinRep/Luc vectors were produced as described below. Briefly, the plasmids carrying the SinRep/Luc replicon or DHBB helper RNAs were linearized with Xho I and Not I respectively. The linearized DNAs were subject to in vitro transcription using the mMESSAGE mMACHINE™ RNA transcription kit (SP6 version, Ambion Inc., Austin, Tex.) to produce capped mRNA transcripts. Both helper and replicon RNAs (20 µL each of the in vitro transcription reaction mix) were electroporated into BHK cells as described[2]. Electroporated cells were incubated in 10 mL of aMEM containing 5% FBS at 37° C. for 12 hr. Then the medium was replaced with 10 mL of Opti-MEM I medium (GIBCO-BRL) without FBS. After 24 hr, culture supernatants were collected and stored at −80° C. The titer of SinRep/Luc vector was determined as described previously 2.

Animal Models

All experiments used female, 6-8 week old, severe combined immunodeficient mice (strain C.B-17-SCID), obtained from Taconic (Germantown, N.Y.). All animal experiments were performed in accordance with NIH and institutional guidelines.

To induce s.c. tumors, $1 \times 10^6$ BHK cells were injected s.c. to C.B-17-SCID mice on the right flank of the lower abdomen. After 12 days, when the BHK tumors had reached a size of at least 500 mm$^3$, the mice were randomly assigned to a control (n=5) and a SinRep/Luc (n=5) group, and the treatment was started on that day (day 1). SinRep/Luc group received daily i.p. injections on the left flank of the lower abdomen consisting of 0.5 mL of Opti-MEM I containing $10^7$~$10^8$ CFU of SinRep/Luc vectors. Control mice received 0.5 mL of Opti-MEM I. Bioluminescence in mice was monitored on days 5, 10 and 15, using the IVIS system (see below). The size of BHK tumors was determined daily with caliper using the formula: (length, m)×(width, m)×(height, m). Tumor size data was analyzed with two-way ANOVA using GraphPad Prism version 3.0a for Macintosh (GraphPad Software, San Diego, Calif.) as described 2.

To induce intrapancreatic tumors, C.B-17-SCID mice were anesthetized followed by intrapancreatic injection of $1 \times 10^6$ BHK or BHKSINLuc2 cells with 21-gauge syringes. When infected with Sindbis virus or Sindbis vectors, BHKSINLuc2 cells produce luciferase activity. Eight days after tumor inoculation, 0.5 mL SinRep/Luc or SinRep/LacZ vectors (~$10^7$ CFU) was injected i.p. into mice bearing BHK or BHKSINLuc cells respectively. Next day the mice were monitored for bioluminescence using the IVIS® system (described below). Mice were euthanized the day after imaging to document tumor growth photographically.

To obtain lung tumors, $1 \times 10^6$ BHK cells were injected via the tail vein. Seven days later, mice were injected i.v. with 0.5 mL SinRep/Luc vectors (~$10^7$ CFU) via tail vein for two consecutive days. Control mice were not inoculated with BHK cells, but were treated with SinRep/Luc vector in parallel with experimental mice. Next day luciferase activity was monitored within experimental and control mice using the IVIS imaging system. Mice were euthanized the day after imaging and tumor growth documented photographically.

To establish the advanced ovarian cancer model, C.B-17-SCID mice were i.p. injected with $2 \times 10^6$ ES-2 cells in 0.5 mL Dulbecco's modified Eagle medium (DMEM) supplemented with 10% FBS. To determine tumor specific infection of Sindbis vectors, mice were treated with a single i.p. injection of SinRep/Luc five days after ES-2 inoculation, and the in vivo bioluminiscence of tumor cells was determined using the IVIS® Imaging System. To determine early disease progress, $1 \times 10^6$ ES-2/Luc cells were i.p. injected in mice which were monitored with IVIS® Imaging System 5 days after ES-2/Luc inoculation.

IVIS® Bioluminescence Imaging

A cryogenically cooled IVIS® system was used (Xenogen Corp., Alameda, Calif.) with a LivingImage acquisition and analysis software (Xenogen Corp.) to detect the bioluminescence signals in mice. Each mouse was injected i.p. with 0.3 mL of 15 mg/mL beetle luciferin (potassium salt; Promega Corp., Madison, Wis.) in PBS. After 5 min, mice were anesthetized with 0.3 mL of Avertin (1.25% of 2,2,2-tribromoethanol in 5% tert-amyl alcohol). The imaging system first took a photographic image in the chamber under dim illumination, followed by luminescent image acquisition. The overlay of the pseudocolor images represents the spatial distribution of photon counts produced by active luciferase. An integration time of 1 min with a binning of 2 pixels was used for luminescent images acquired from BHK s.c. tumors, and 5 min for lung tumors. For s.c BHK tumor models, the LivingImage software (Xenogen Corp.) was used to integrate the total bioluminescence signals (in terms of photon counts) from tumors after SinRep/Luc treatments.

Histological Analysis

Tissues were harvested from mice and fixed in 10% neutral buffered formalin for at least 12 hr and then embedded in paraffin. Sections were prepared onto electrostatically charged glass slides, then baked at 60° C. overnight. After deparaffinization with three washes in xylene, the sections were rehydrated through a series of graded ethanols (100%, 90%, and 70%) prior to hematoxylin and eosin staining.

Example 1

SinRep/Luc Viral Vector Specifically Infects Subcutaneous (s.c.) BHK Tumors and Suppresses Their Growth To test the potential of Sindbis viral vectors for systemic delivery and specific infection, a SinRep/Luc viral vector was injected daily, which carries a firefly luciferase gene, intraperitoneally (i.p.) to SCID mice bearing s.c. BHK tumors (FIG. 1). The daily i.p. injections of SinRep/Luc vectors was started when the tumors were approximately 500 mm$^3$ (day 1) and the IVIS® system was used to monitor bioluminescence in the mice on days 5, 10, and 15. Control tumor-bearing mice received no SinRep/Luc treatment. On day 5, tumor specific bioluminescence that persisted until day 10 and dropped significantly on day 15 (P=0.0004, student t-test, FIG. 1a) was observed. S.c. BHK tumors on control mice generated very low background bioluminescence signals (~$10^3$ photon counts) compared with SinRep/Luc treated tumors (~$10^7$ photon counts). By day 10, a substantial therapeutic effect of Sindbis vector was clear as evidenced by size differences between treated and control tumors (FIG. 1b). Specificity for tumor cells was demonstrated by the lack of substantial bioluminescence signal in other regions of the treated mice. In some experiments, particularly after multiple infections, low levels of bioluminescence signals at the sites of vector injections were also observed after day 10, which was attributed to some vector retention at these sites (data not shown). Two-way ANOVA analysis of tumor sizes revealed that SinRep/Luc treatment had completely inhibited the s.c. tumor growth (P<0.0001, FIGS. 1b and c).

Figure 1D:
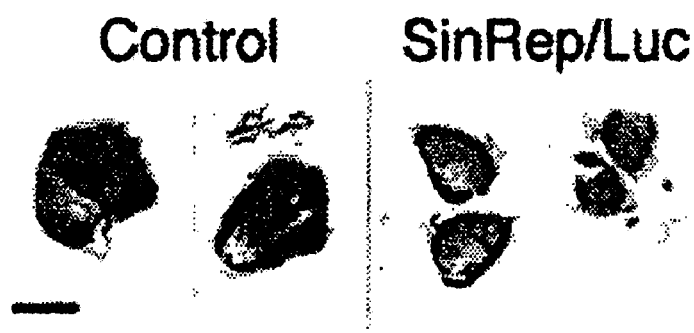
Figure 1E:
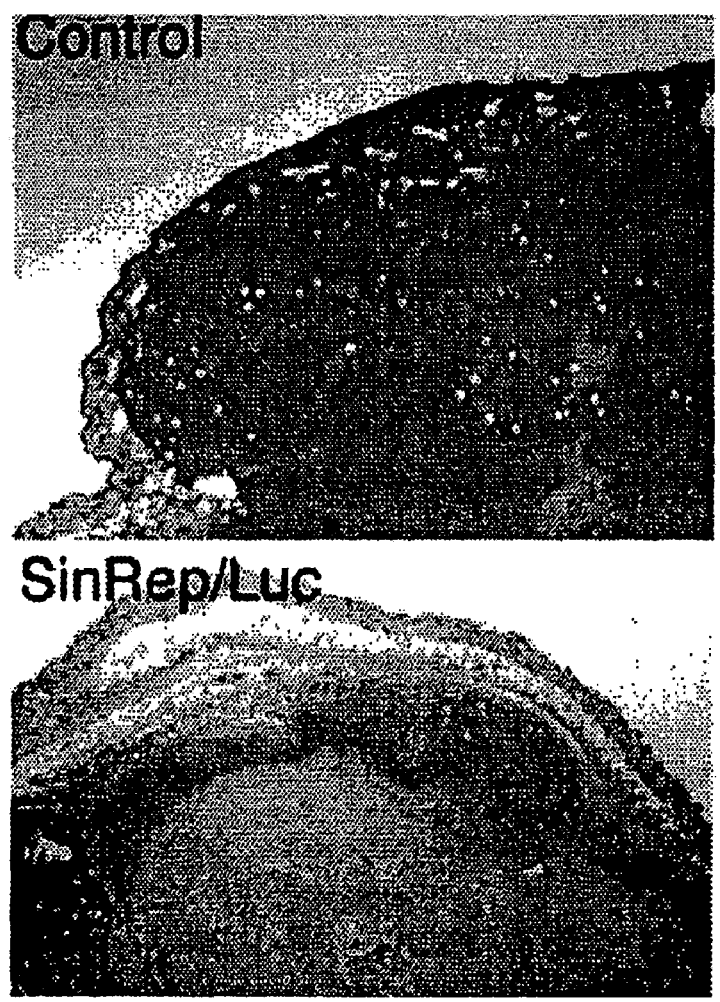

Since all treated tumors had ceased growing and displayed little bioluminescence by day 15, whether the reduction of bioluminescence signals resulted from tumor necrosis induced by Sindbis-mediated apoptosis was examined. Histopathology studies demonstrated that this was the case; hematoxylin and eosin staining of harvested tumor sections indicated that, in addition to the size differences, the treated tumors had a greater proportion of necrotic areas than untreated control tumors (FIG. 1d). Further, most of the treated tumors were homogeneously necrotic except at the very outer rims where there were viable tumors (FIG. 1e). In contrast, the necrotic areas in control tumors were smaller in size and more irregular in shape, as would be expected from normal tumor associated phenomena such as hypoxia and poor nutrition (FIG. 1e). In addition, previous immunostaining data indicated that s.c. tumors infected with the Sindbis vectors regress completely within three to four weeks of treatment and tumor death is the result of apoptosic infection associated with areas of the vasculature[8].

Example 2

Figure 2A:
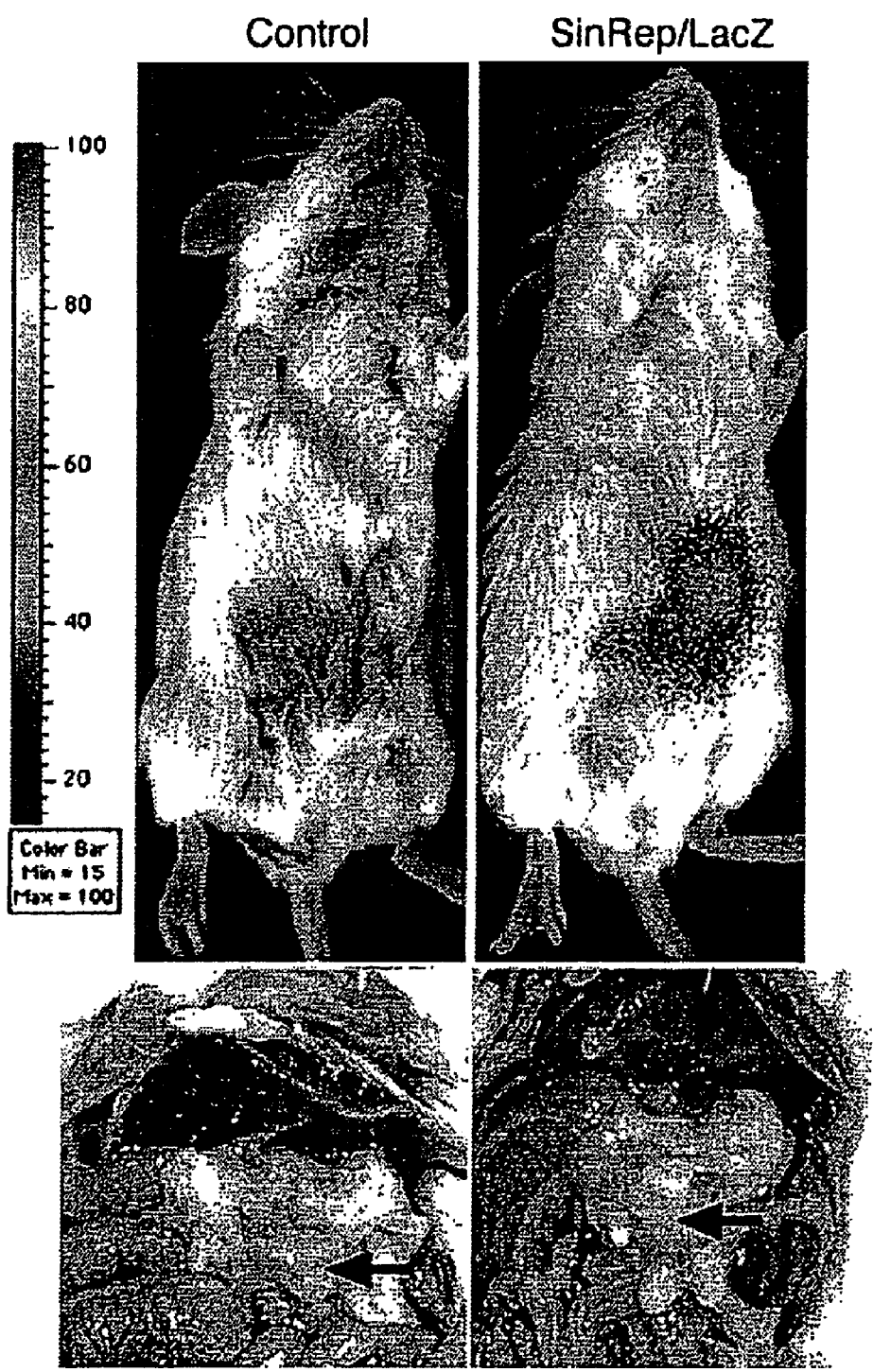
FIGS. 2(A-C) Single i.p. delivery of SinRep/LacZ vectors specifically infected intrapancreatic BHKINLuc2 tumors and induced their luciferase activities as determined by the IVIS® Imaging System. a, Mice carrying an intrapancreatic BHKSINLuc2 tumor showed substantial bioluminescence signal in the pancreas after a single i.p. treatment of SinRep/LacZ vectors (upper panels). The specific infection of intrapancreatic tumors induced the luciferase activity of BHKSINLuc2 cells. In contrast, control tumor-bearing mice that received no SinRep/LacZ treatment showed no background bioluminescence signal in the pancreas. Surgical examination at autopsy confirmed the presence of intrapancreatic BHKSINLuc2 tumors in both control and SinRep/LacZ treated mice as indicated by arrows (lower panels). b, Immunohistologic staining confirmed tumor-specific infection of SinRep/LacZ vectors to intrapancreatic BHKSINLuc2 tumors. Arrow # 1 and arrow # 2 indicate normal pancreatic tissue and BHKSINLuc2 tumor cells respectively. Intrapancreatic BHKSINLuc2 tumor sections were harvested from mice untreated (control) or treated with SinRep/LacZ vectors as shown in a. Consecutive sections (5 μm apart) were stained with standard hematoxylin/eosin (left), or with a monoclonal antibody specific to the LacZ gene product, bacterial f-galactosidase (right), for immunohistologic staining. All BHKSINLuc2 tumor regions within pancreas are positive for SinRep/LacZ infection as determined by the f-galactosidase staining. Magnification: control (100×), SinRep/LacZ (20×). c, The boxed regions in FIG. 2b at higher magnifications (200×). Control slide indicate no positive β-galactosidase signal in either tumor or normal pancreas tissues. By contrast, in the pancreas sections obtained from mice treated with SinRep/LacZ vectors, strong β-galactosidase signals exclusively presented in tumor regions and formed a sharp border between tumor and normal pancreatic tissues, which had no positive β-galactosidase signal.

Sindbis Viral Vectors Specifically Infect Intraperitoneal (i.p.) and Intrapancreatic BHK Tumors To determine if Sindbis vectors can specifically infect BHK tumors growing at other locations, intrapancreatic tumors were established with a special BHK-derived line, BHKSINLuc2, which stably transcribes a defective Sindbis replicon RNA containing a firefly luciferase gene[31]. Since this cell line expresses luciferase activity in response to Sindbis infection, BHKSINLuc2 tumors as biological reporters of vector infection were used. Intrapancreatic inoculation of $1\times10^6$ BHKSINLuc2 cells resulted in tumors mostly limited to the pancreas after eight days. A single i.p. injection of a Sindbis vector SinRep/LacZ that carries a bacerial β-galactosidase gene, led to specific infection of the intrapancrestic BHKSINLuc2 tumors and induction of luciferase activities (FIG. 2a, upper panels). Without SinRep/LacZ treatment, the control mice bearing intrapancreatic BHKSINLuc2 tumor showed no bioluminescence signal in the pancreas. The presence of tumors in both control and treated pancreases was confirmed by autopsy after imaging (FIG. 2a, lower panels).

Figure 2B:
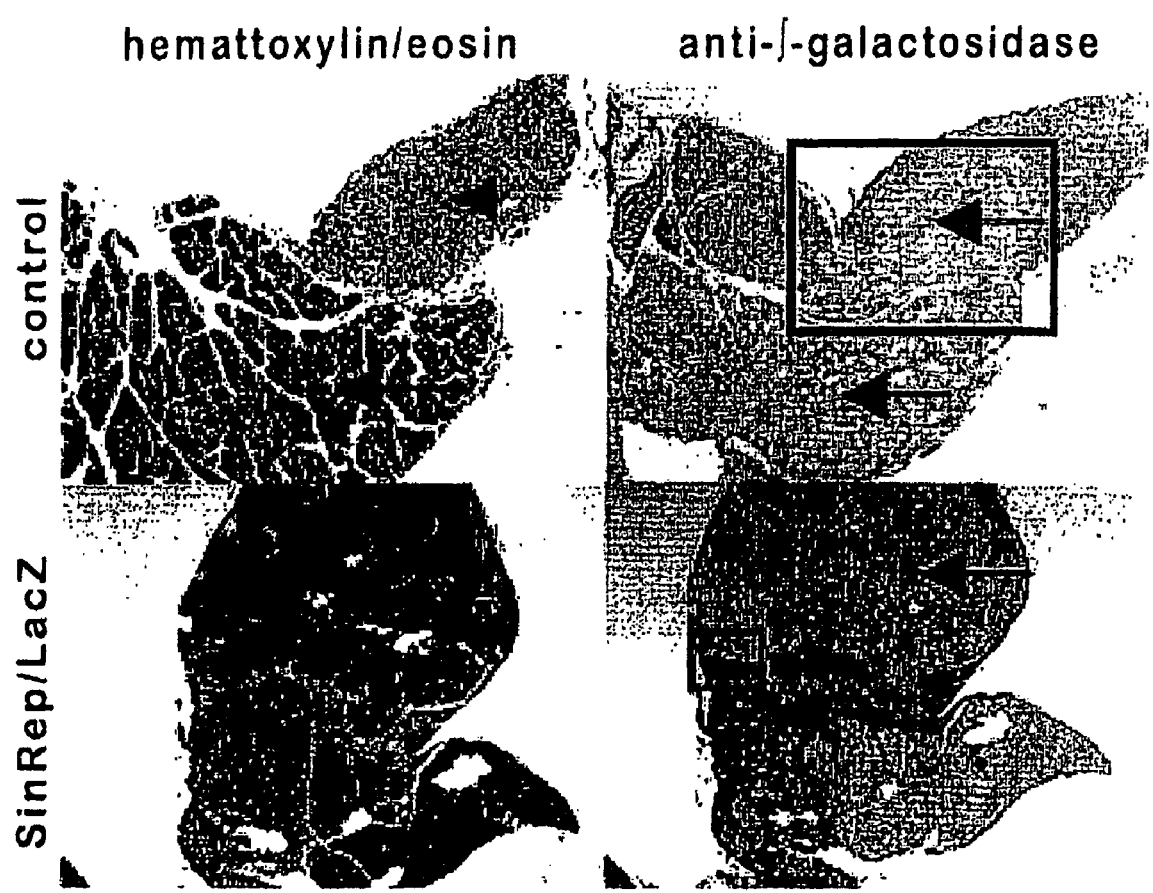
Figure 2C:

The IVIS® Imaging System provides the ability to follow viral infection events in vivo, and truly reflects the remarkable targeting capabilities of Sindbis vectors, which can be appreciated even more fully by examining specific vector infection of intrapancreatic tumors using immunohistochemical analysis of the imaged animal (Fig. b). It is evident from the tissue sections that tumor invasion of the pancreas is extensive (FIG. 2b, lower left panel, lighter areas of tissue section are comprised of tumor cells). Remarkably, after a single systemic administration of Sindbis vectors (SinRep/LacZ) encoding the bacterial β-galactosidase, only tumor areas of the pancreas stain with an antibody specific to β-galactosidase and virtually all tumor cells are positive for β-galactosidase staining as a result of vector infection (FIG. 2b, lower right panel, brown areas). It is evident that areas of Sindbis infection are superimposable with tumor area on the slide. The virtually complete tumor infection is visualized even more clearly at height magnifications (FIG. 2c, bottom panel). These immunohistochemical pictures explain why Sindbis vectors are effective at eradicating tumors. They infect and kill virtually all tumor cells without affecting normal cells.

Example 3

Sindbis Vectors Specifically Infected Intraperitoneal Metastasized Tumors

Figure 3A:
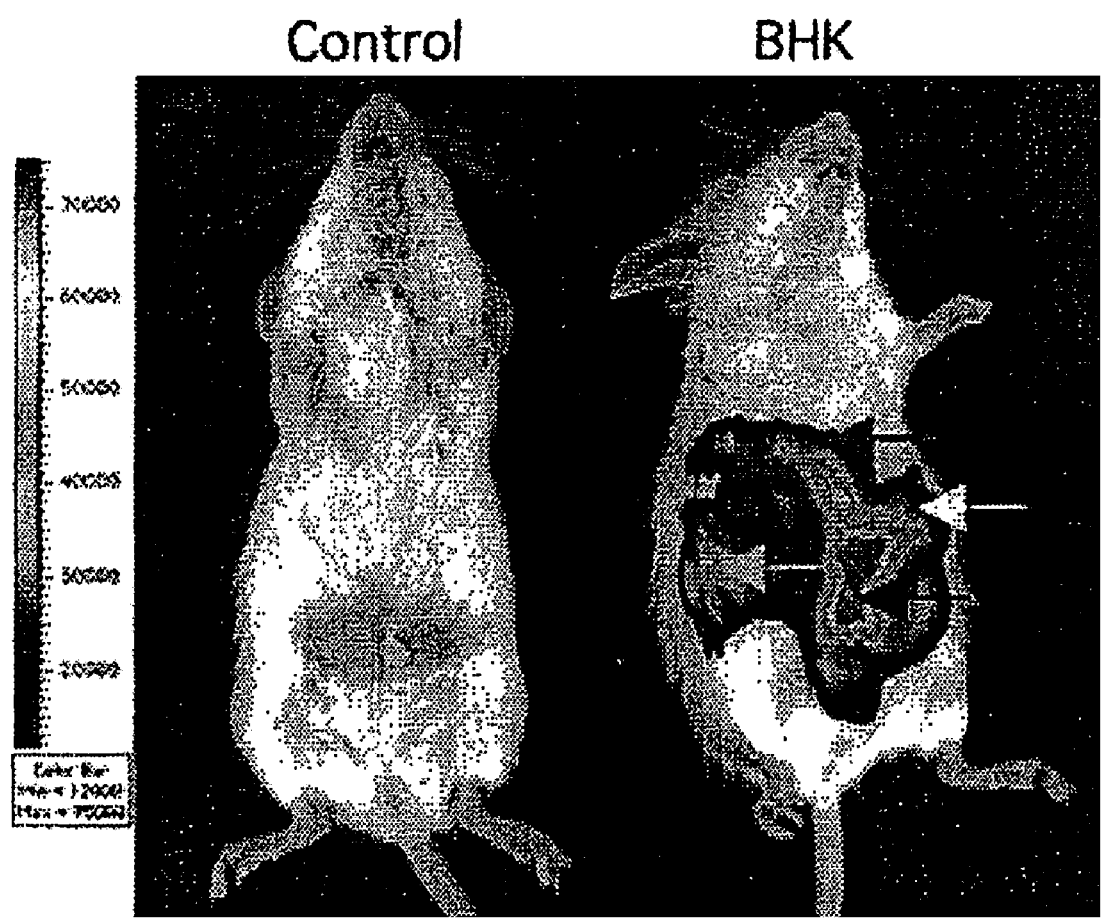
FIGS. 3(A and B) I.p. delivery of SinRep/Luc specifically infects disseminated BHK tumors in the peritoneal cavity. a, In addition to tumor growth in the pancreas, intrapancreatic injection of BHK cells results in tumor dissemination throughout the peritoneal cavity. Single i.p. delivery of SinRep/Luc vector specifically infects the disseminated BHK tumor as determined by IVIS® imaging. Tumor-free control mice that received a single i.p. SinRep/Luc injection showed no substantial background bioluminescence. Arrows #1, #2, #3 and #4 indicate the bioluminescence signal on diaphragm, pancreas, mesentery and peritoneum respectively. b, Examination at autopsy confirmed the tumor presence on diaphragm (arrow # 1), pancreas (arrow # 2), mesentery (arrow # 3), and peritoneum (arrow # 4) of the SinRep/Luc-treated mouse imaged in a. No tumor was present in control mouse.
Figure 3B:
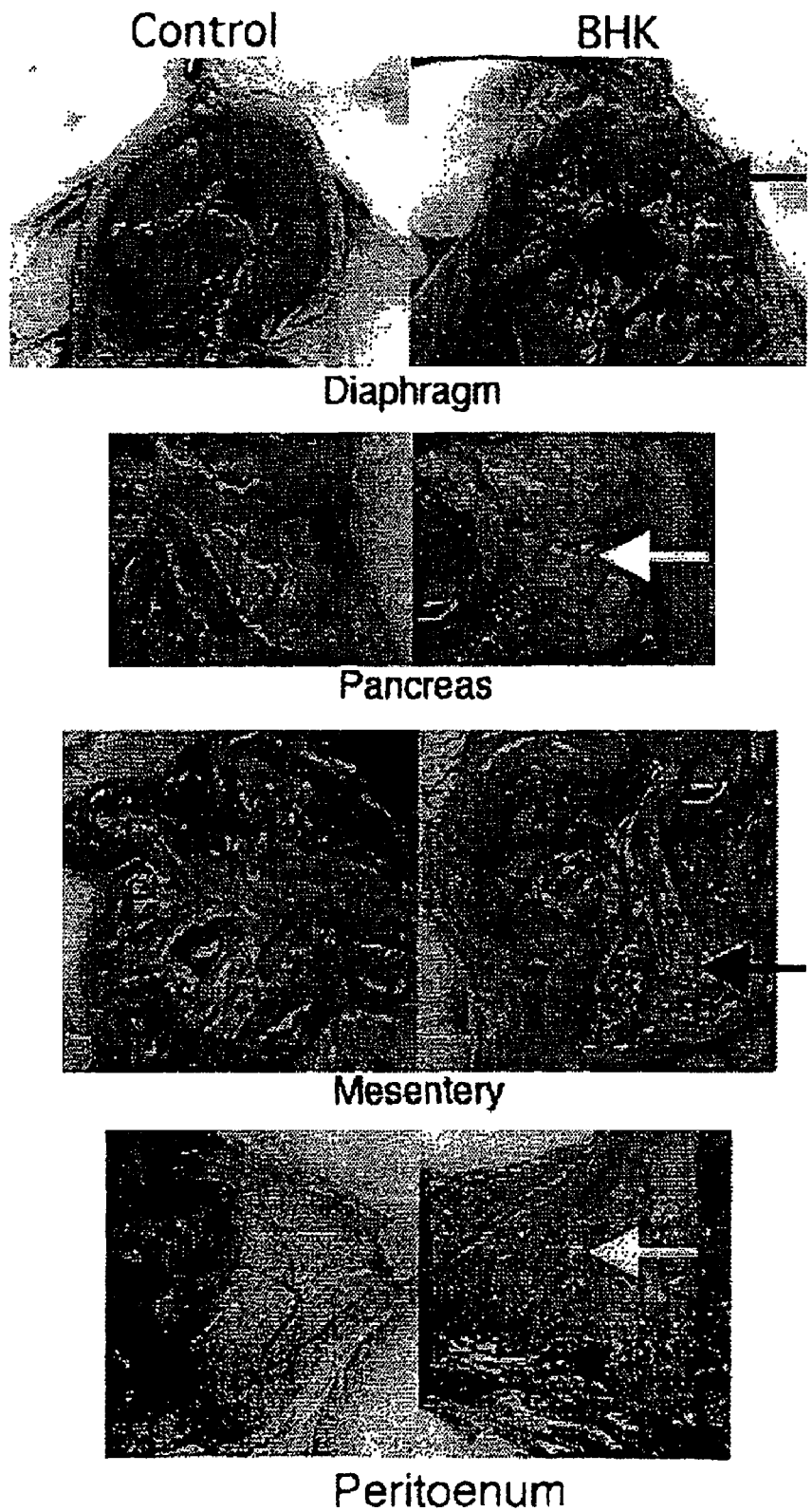

In another set of experiments, $1\times10^6$ BHK cells were intrapancreatically inoculated in SCID mice. Intrapancreatic BHK tumors grew faster than BHKSINLuc2 tumors and resulted in metastasis throughout the peritoneal cavity (FIG. 3). Eight days after BHK cell inoculation, a single i.p. injection of SinRep/Luc vectors to mice induced specific and substantial bioluminescence signals (FIG. 3a) associated with tumor development on the diaphragm, pancreas, mesentery, and peritoneum (FIG. 3b). Background bioluminescence signals were minimal in the peritoneal cavity of tumor-free control mice that were given a single i.p. SinRep/Luc vector injection (FIG. 3a).

These results indicate that single i.p. delivery of Sindbis vectors can specifically infect the metastasized BHK tumors throughout the peritoneal cavity. Thus, Sindbis vectors, while delivered systemically, may serve as powerful tools for detecting microscopic metastasized tumors throughout the peritoneal cavity, a typical symptom observed in human advanced ovarian cancer.

Example 4

SinRep/Luc Vector Specifically Detects Micrometastitic I.P. Tumors

To examine this result further, the ability of Sindbis vectors for specific infection of microscopic tumors was tested in an established murine advanced ovarian cancer model, which is achieved by i.p. inoculation of ES-2 human ovarian cancer cells. Five days after i.p. inoculation of $2\times10^6$ ES-2 cells, no gross tumor growth in the peritoneal cavity was visible except for few small (~2 mm) unattached tumor clusters. However, microscopic tumor metastases can be readily detected on omentum, mesentery and diaphragm at this early stage of disease progress (FIG. 4a). To detect the metastases of ES-2 cells at this early stage of advanced disease, an ES-2 cell line, ES-2/Luc that stably expresses the luciferase gene in the absence of vector infection was genreated. As determined with the IVIS® imaging System, i.p. injection of $1\times10^6$ ES-2/Luc cells induced the same pattern of disease progress in 5 days after inoculation (FIG. 4b) as injection of ES-2 cells. However, compared to gross and microscopic examination of mice, ES-2/Luc cells permitted earlier detection of tumor growth and did so without the need to sacrifice the test animals. A single i.p. injection of SinRep/Luc vectors to mice bearing ES-2 cancers at this early stage disease, allowed for the detection of bioluminescence signals on omentum, mesentery and diaphragm comparable to those seen in the ES-2/Luc injected mice (FIG. 4b).

This observation demonstrates that Sindbis vectors are capable of targeting and infecting microscopic tumors in the peritoneal cavity, and that the vectors can be used in this manner to identify micrometastases. Given the remarkable specificity of Sindbis vectors for a wide range of tumors, these vectors when combined with a variety of reporter genes suitable for imaging[32] have the previously unrecognized potential to serve as tools to identify micrometastases.

Figure 4C:
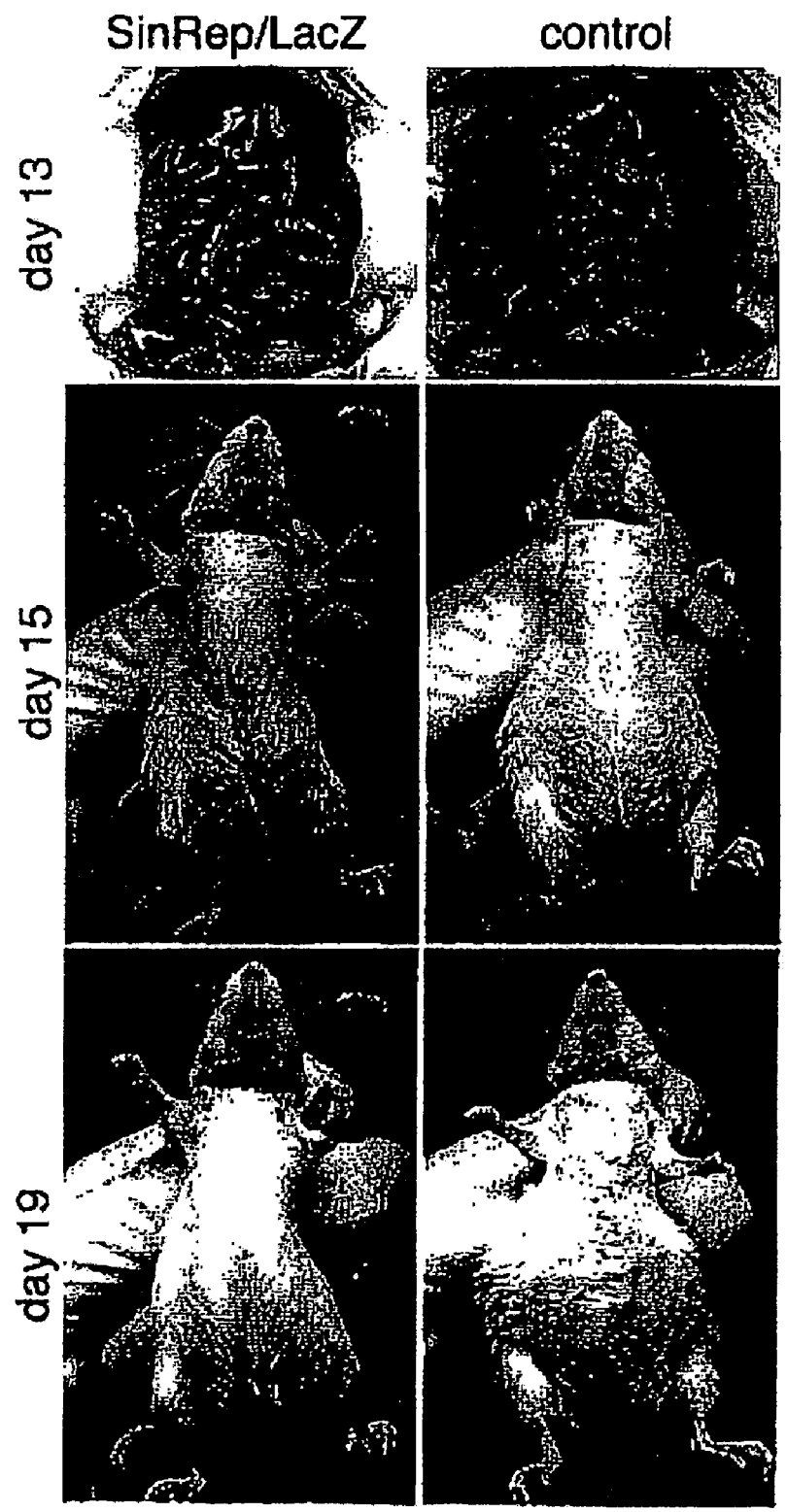
FIGS. 4(A B and C) I.p. treatment with SinRep/Luc specifically infected microscopic metastasized ES-2 ovarian tumors in the peritoneal cavity and significantly suppressed disease progress. a, Microscopic metastasized ES-2 tumors (indicated by arrows, magnification: 100×) were observed in omentum (left), mesentery (middle) and diaphragm (right) 5 days after i.p. inoculation with $2 \times 10^6$ ES-2 cells. b, 5 days after i.p. ES-2 inoculation, while the tumor growth was still microscopic throughout peritoneal cavity, single i.p. treatment of SinRep/Luc vectors is sufficient to specifically infect microscopic metastasized ES-2 cells on omentum (indicated by arrow # 1), mesentery (indicated by arrow #2) and diaphragm (indicated by arrows # 3) as determined by the IVIS® Imaging System the day after vector treatment. Mice i.p. injected with $1 \times 10^6$ ES-2/Luc cells, which stably express firefly luciferase activities, showed similar tumor growth pattern on omentum, mesentery and diaphragm 5 days after inoculation. Tumor-free control mice show no substantial bioluminescence signal after receiving single i.p. SinRep/Luc treatment. c, The daily treatments significantly suppressed the disease progress as indicated by reduced ascites development. Mice were i.p. inoculated with $2 \times 10^6$ ES-2 cells on day 0, and, on day 5, daily i.p. injections of SinRep/LacZ vectors or Opti-MEM I medium (control) was started. On day 13, control mice develop grossly visible ascites; however, while SinRep/LacZ treated mice show no visible ascites development. Without treatment, rapid ascites development was observed in untreated control mice from day 15 to day 19.

Beyond imaging the therapeutic effects of the vector in this advanced ovarian cancer model was explored. As expected, daily Sindbis vector treatment of mice in the early stages of advanced ovarian cancer significantly suppressed disease progression, as determined by inhibition of ascites development (FIG. 4c), which are a major clinical manifestation of this disease, and prolong survival (median survival: untreated control=18 days, SinRep/LacZ=25 days, P<0.0001). About 18 days after ES-2 tumor inoculation, ~'80% of untreated mice die from the disease and show numerous tumor metastasis to the bowel, omentum, and diaphragm along with severe ascites (FIG. 4c). By day 20, ~'5% untreated mice are dead.

By contrast, no ascites are visible in Sindbis treated mice over the first 19 days (FIG. 4c). The start of liver tumor growth in SinRep/LacZ treated mice was not observed until day 23. However, although tumor growth in treated mice is significantly delayed and suppressed, it is not eradicated. In this very aggressive model of advanced ovarian cancer all mice, treated or untreated, eventually succumb to the disease.

Example 5

SinRep/Luc Infected Lung-Metastasized Tumors via the Bloodstream

Figure 5A:
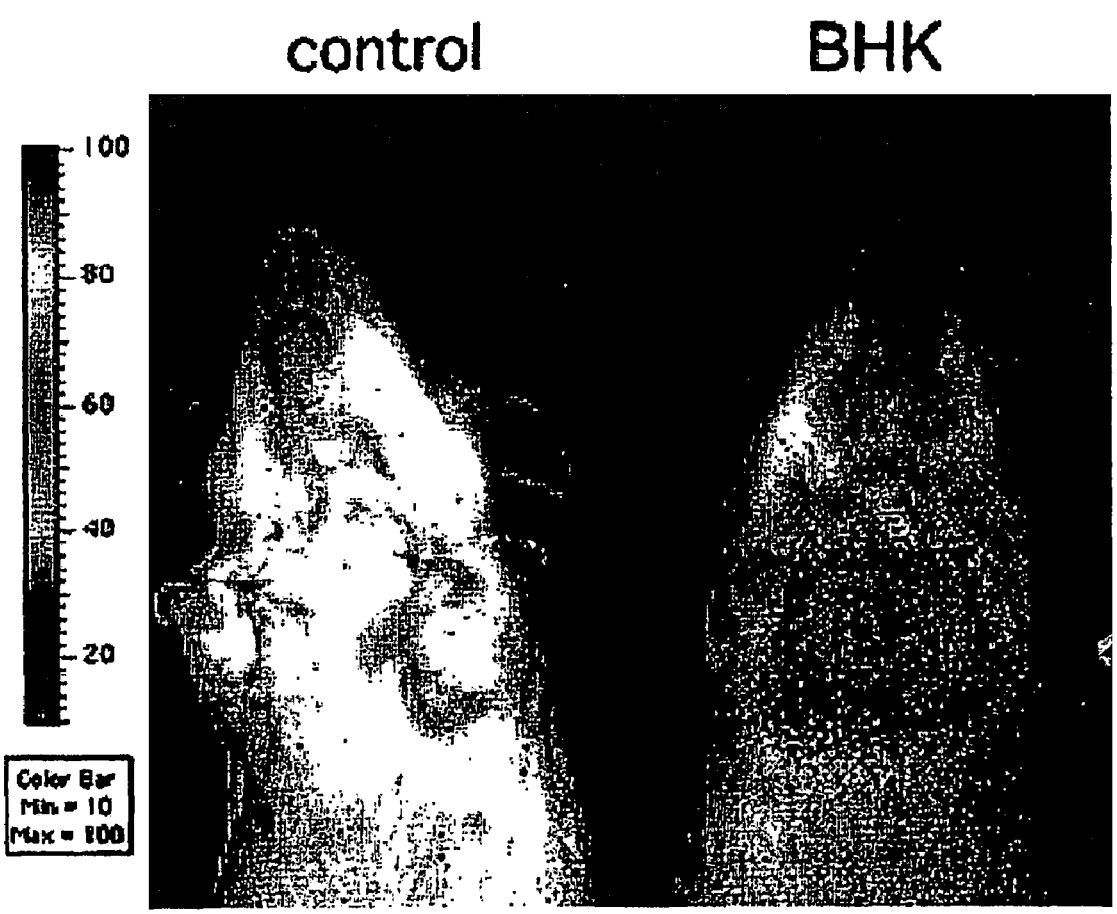
FIGS. 5(A, B and C) Intravenous (i.v.) delivery of SinRep/Luc vectors targeted BHK tumor in lung, which is induced by i.v. injection of BHK cells. a, IVIS® imaging showed that i.v. injections of SinRep/Luc vector result in significant bioluminescence signals in mice that carried BHK tumors in lungs. Tumor-free control mice show no bioluminescence signal. b, Surgical examination after imaging showed the presence of tumor in lungs of mice previously i.v. inoculated with BHK cells but not in control mice. Bar: 10 mm. c, Microscopically, the presence of BHK tumor cells is confirmed by hematoxylin/eosin staining of lung sections obtained from tumor-free control or BHK-injected mice. The arrow indicates tumor cells in lungs of a BHK-injected mouse. No tumor existed in the lungs of control mice. Magnification: control (200×), BHK (100×).
Figure 5B:
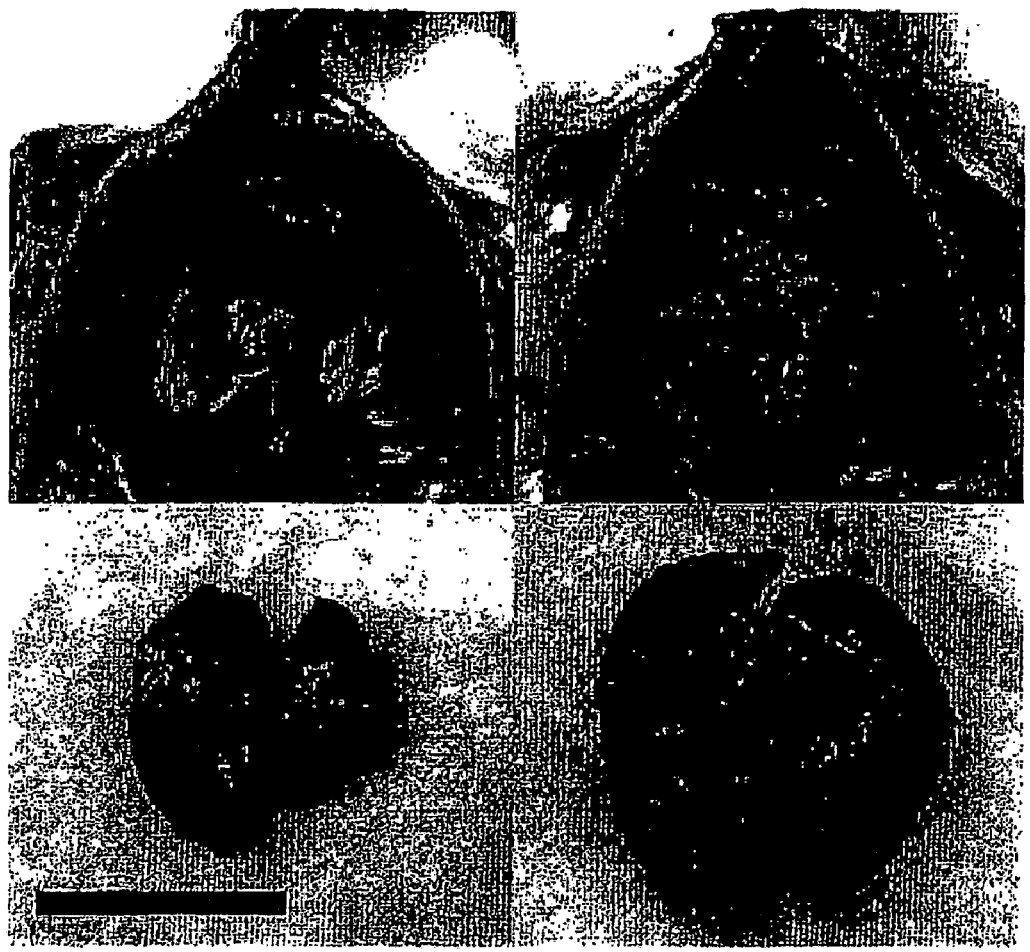
Figure 5C:
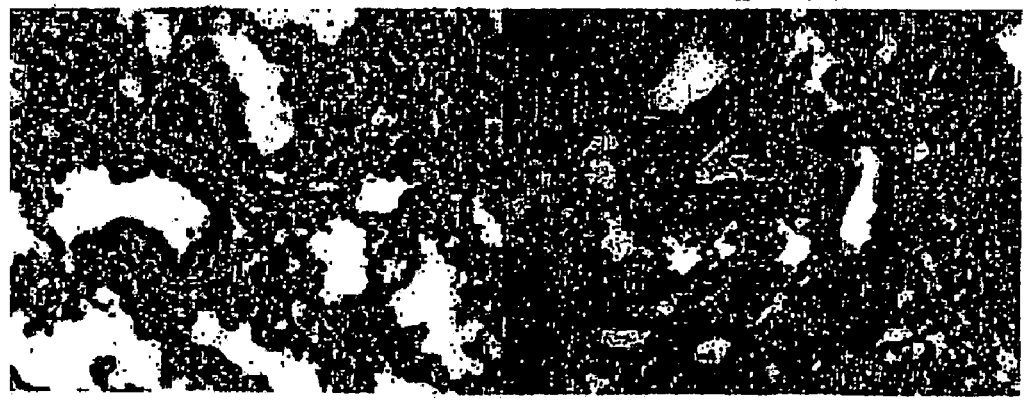

To further confirm the ability of blood-borne Sindbis vector for systemic detection of metastasized tumors, the IVIS® Imaging System was used to determine specific vector targeting to tumors induced in the lungs. Intravenous inoculation of $1 \times 10^6$ BHK cells results in growth of tumor cells in the lungs (FIG. 5). Seven days after inoculation, when animals display tumor-related symptoms such as dypsnea, SinRep/Luc vectors were injected i.v. for two consecutive days. Tumor-free control mice also received two consecutive SinRep/Luc treatments. On the day following the second SinRep/Luc treatment, substantial bioluminescence signals were observed in the chest of the BHK-injected mice but not in the control mice (FIG. 5a). After imaging, lung metastases and tumor growth of BHK-injected mice were confirmed by autopsy (FIG. 5b) and histologic analysis (FIG. 5c).

REFERENCES

1. Bredenbeek, P. J., Frolov, I., Rice, C. M. & Schlesinger, S. Sindbis virus expression vectors: packaging of RNA replicons by using defective helper RNAs. *J Virol* 67, 6439-6446. (1993).
2. Tseng, J. C. et al. In vivo antitumor activity of sindbis viral vectors. *J Natl Cancer Inst* 94, 1790-1802. (2002).
3. Strauss, J. H. & Strauss, E. G. The alphaviruses: gene expression, replication, and evolution. *Microbiol Rev* 58, 491-562. (1994).
4. Ryman, K. D., Klimstra, W. B., Nguyen, K. B., Biron, C. A. & Johnston, R. E. Alpha/beta interferon protects adult mice from fatal Sindbis virus infection and is an important determinant of cell and tissue tropism. *J Virol* 74, 3366-3378. (2000).
5. Cook, S. H. & Griffin, D. E. Luciferase imaging of a neurotropic viral infection in intact animals. *J Virol* 77, 5333-5338. (2003).
6. Wang, K. S., Kuhn, R. J., Strauss, E. G., Ou, S. & Strauss, J. H. High-affinity laminin receptor is a receptor for Sindbis virus in mammalian cells. *J Virol* 66, 4992-5001. (1992).
7. Strauss, J. H., Wang, K. S., Schmaljohn, A. L., Kuhn, R. J. & Strauss, E. G. Host-cell receptors for Sindbis virus. *Arch Virol Suppl* 9, 473-484. (1994).
8. Martignone, S. et al. Prognostic significance of the 67-kilodalton laminin receptor expression in human breast carcinomas. *J Natl Cancer Inst* 85, 398-402. (1993).
9. Sanjuan, X. et al. Overexpression of the 67-kD laminin receptor correlates with tumour progression in human colorectal carcinoma. *J Pathol* 179, 376-380. (1996).
10. de Manzoni, G. et al. Study on Ki-67 immunoreactivity as a prognostic indicator in patients with advanced gastric cancer. *Jpn J Clin Oncol* 28, 534-537. (1998).
11. Taraboletti, G., Belotti, D., Giavazzi, R., Sobel, M. E. & Castronovo, V. Enhancement of metastatic potential of murine and human melanoma cells by laminin receptor peptide G: attachment of cancer cells to subendothelial matrix as a pathway for hematogenous metastasis. *J Natl Cancer Inst* 85, 235-240. (1993).
12. Ozaki, I. et al. Differential expression of laminin receptors in human hepatocellular carcinoma. *Gut* 43, 837-842. (1998).
13. van den Brule, F. A. et al. Expression of the 67 kD laminin receptor in human ovarian carcinomas as defined by a monoclonal antibody, MLuC5. *Eur J Cancer* 32A, 1598-1602. (1996).
14. van den Brule, F. A. et al. Differential expression of the 67-kD laminin receptor and 31-kD human laminin-binding protein in human ovarian carcinomas. *Eur J Cancer* 30A, 1096-1099. (1994).
15. Liebman, J. M., Burbelo, P. D., Yamada, Y., Fridman, R. & Kleinman, H. K. Altered expression of basement-membrane components and collagenases in ascitic xenografts of OVCAR-3 ovarian cancer cells. *Int J Cancer* 55, 102-109. (1993).
16. Menard, S., Tagliabue, E. & Colnaghi, M. I. The 67 kDa laminin receptor as a prognostic factor in human cancer. *Breast Cancer Res Treat* 52, 137-145. (1998).
17. Viacava, P. et al. The spectrum of 67-kD laminin receptor expression in breast carcinoma progression. *J Pathol* 182, 36-44. (1997).
18. Liotta, L. A. Tumor invasion and metastases—role of the extracellular matrix: Rhoads Memorial Award lecture. *Cancer Res* 46, 1-7. (1986).
19. Aznavoorian, S., Murphy, A. N., Stetler-Stevenson, W. G. & Liotta, L. A. Molecular aspects of tumor cell invasion and metastasis. *Cancer* 71, 1368-1383. (1993).
20. Levine, B. et al. Conversion of lytic to persistent alphavirus infection by the bcl-2 cellular oncogene. *Nature* 361, 739-742. (1993).
21. Jan, J. T., Chattedjee, S. & Griffin, D. E. Sindbis virus entry into cells triggers apoptosis by activating sphingomyelinase, leading to the release of ceramide. *J Virol* 74, 6425-6432. (2000).
22. Jan, J. T. & Griffin, D. E. Induction of apoptosis by Sindbis virus occurs at cell entry and does not require virus replication. *J Virol* 73, 10296-10302. (1999).
23. Balachandran, S. et al. Alpha/beta interferons potentiate virus-induced apoptosis through activation of the FADD/Caspase-8 death signaling pathway. *J Virol* 74, 1513-1523. (2000).
24. Olivo, P. D., Frolov, I. & Schlesinger, S. A cell line that expresses a reporter gene in response to infection by Sindbis virus: a prototype for detection of positive strand RNA viruses. *Virology* 198, 381-384. (1994).
25. Akporiaye, E. T. & Hersh, E. Clinical aspects of intratumoral gene therapy. *Curr Opin Mol Ther* 1, 443-453. (1999).
26. Griffin, D. E., Levine, B., Tyor, W. R., Tucker, P. C. & Hardwick, J. M. Age-dependent susceptibility to fatal encephalitis: alphavirus infection of neurons. *Arch Virol Suppl* 9, 31-39. (1994).
27. Frolov, I. & Schlesinger, S. Comparison of the effects of Sindbis virus and Sindbis virus replicons on host cell protein synthesis and cytopathogenicity in BHK cells. *J Virol* 68, 1721-1727. (1994).
28. Frolova, E. I. et al. Roles of nonstructural protein nsP2 and Alpha/Beta interferons in determining the outcome of Sindbis virus infection. *J Virol* 76, 11254-11264. (2002).

In Examples 6-11 below, the following materials and methods were used.

Cell Lines

ES-2 cells were obtained from the American Type Culture Collection (ATCC, Manassas, Va.) and were cultured in McCoy's 5A medium (Mediatech, Inc., Herndon, Va.) supplemented with 10% FBS. ES-2/Fluc cells are derived from the ES-2 line by stable transfection of a plasmid, pIRES2-Fluc/EGFP, as described previously (3). A hairpin siRNA sequence targeting 5'-CCAGAUCCAGGCAGC-CUUC-3' (SEQ ID NO: 1) of the human laminin receptor precursor (LRP) transcript was designed using the on-line insert design tool (www.ambion.com, Ambion Inc. Austin, Tex.) and was ligated into the BamHI site on pSilencer™ 2.1-U6 hygro plasmid (Ambion Inc.). The siRNA expression cassette was excised from pSilencer™ 2.1-U6 hygro plasmid using the PvuII restriction enzyme and was sub-cloned into the AflII site on the pIRES2-Fluc/EGFP plasmid. The plasmid, named pIRES2-Fluc/EGFP/aLRP, was then stably transfected into ES-2 cells to generate the ES-2/Fluc/aLRP cell line. The mouse ovarian MOSEC cell line (clone 1D8) was a generous gift from Dr. Katherine F. Roby at University of Kansas Medical Center, Kansas City, and was maintained in Dulbecco's modified Eagle's medium (DMEM) supplemented with 4% FBS and 1×ITS (Insulin-Transferrin-Selenium, Mediatech).

Production of Sindbis Vectors

Various Sindbis vectors were produced by electroporation of both replicon RNA (SinRep5) and helper RNA (DH-BB) into BHK cells as described previously (3). The *Renilla* luciferase (Rluc) gene was excised from the phRL-CMV plasmid (Promega Co., Madison, Wis.) and inserted into the Xba I site of the SinRep5 plasmid (Invitrogen Co., San Diego, Calif.) for Sindbis/Rluc vector production. A similar procedure was performed to generate the Sindbis/IL-15 vector, which carries a mouse IL-15 gene obtained from the pORF-mIL-15 plasmid (InvivoGen Co.).

β-Galactosidase Activity Assay $3 \times 10^5$ ES-2/Fluc or ES-2/Fluc/αLRP cells were infected on 12-well plates with Sindbis/LacZ vectors at multiplicities of infection (MOI) of 100, 10, or 1. After 1 hr incubation at room temperature, cells were washed with PBS and cultured in αMEM/5% FBS. The next day, cells were lysed with 200 μL of M-PER® lysis buffer (Pierce Biotechnology, Rockford, Ill.). 50 μL of the cell lysates were added into 50 μL of All-in-One Beta-Galactosidase Assay Reagent (Pierce Biotechnology) and incubated at room temperature for 5 min prior to reading at 405 nm. For each designed MOI three independent assays were performed and the data presented as the percentage of activities compared with infected ES-2/Fluc cells.

Animal Models

C.B-17-SCID mice (female, 6-8 week old, Taconic, Germantown, N.Y.) were i.p. injected with $2 \times 10^6$ ES-2 cells in 0.5 mL McCoy's 5A medium on day −5. On day 0, both ES-2 inoculated mice and tumor-free control mice received a single treatment of Sindbis/Fluc vector and the bioluminescence signals were monitored using the IVIS® system 100 series (Xenogen Corp., Alameda, Calif.) the next day (day 1) as described previously (3). Some mice received a second i.p. treatment of Sindbis/Fluc vector on day 2 and were IVIS® imaged again on day 3.

For colocalization experiments, SCID mice were i.p. inoculated with $1.5 \times 10^6$ ES-2/Fluc cells on day 0 and received one i.p. treatment of Sindbis/Rluc vector (~$10^7$ PFU in 0.5 mL of OptiMEM I) on day 5. The next day (day 6), the Rluc activities in anesthetized mice was determined by i.p. injection of 0.3 mL of 0.2 mg/mL coelenterazine (Biotium, Inc., Hayward, Calif.) followed by a 5 min IVIS® imaging duration. The bioluminescence generated by Rluc is short-lived and gradually fades away within 30 min (19). After 30 min, the same mice were i.p. injected with 0.3 mL of 15 mg/mL D-luciferin (Biotium, Inc) and a second IVIS® imaging for Fluc activity was performed. LIVING IMAGE® software (Xenogen Corp.) was used to grid the imaging data and integrate the total bioluminescence signals in each boxed region.

$1 \times 10^7$ murine MOSEC cells were injected into C57BL/6 mice (female, 6-8 week old, Taconic, Germantown, N.Y.) to induce advanced ovarian cancer (18). 4 weeks after inoculation, mice were i.p. treated with Sindbis/Fluc and were imaged with IVIS® system the next day. Tumor-free control mice were treated with SinRep/Fluc and imaged in parallel. In order to visualize the specific targeting of Sindbis/Fluc to MOSEC metastases, the tumor-bearing mice were i.p. treated 7 weeks after tumor inoculation and imaged the next day. All animal experiments were performed in accordance with NIH and institutional guidelines.

Tissue Sections and Slide Preparation

Hematoxylin and eosin staining of tissue sections were performed as described previously (3). Immunohistochemistry was performed on formalin fixed paraffin embedded tissues for LAMR detection. Tissue sections (5 μm thick) were prepared onto charged glass slides, baked for 2 hours at 40° C. They were deparaffinized and rehydrated in a phosphate buffered saline solution. Antigen retrieval was performed by boiling in 1 mM EDTA (pH=8) buffer solution for 10 minutes. Tissue sections were incubated with the polyclonal rabbit primary antibody AB711 (1:100 dilution, Abcam Ltd., Cambridge, UK) at room temperature overnight. Detection was performed using an alkaline phosphatase system (VECTASTAIN® ABC-AP kit, Vector laboratories, Burlingame, Calif.) with the secondary antibody diluted at 1:250 and sections were incubated at room temperature for 30 minutes. Hematoxylin was used as a counter stain.

Real-Time RT-PCR 1000, 500, or 250 ng of total cellular RNA obtained from ES-2/Fluc or ES-2/Fluc/αLRP cells was reverse-transcribed (RT) into cDNA for 1 hr at 42° C. in a 20 μL reaction mixture containing 15 units of THERMOSCRIPT™ RNAse H⁻ Reverse Transcriptase (Invitrogen Co.). Real-time quantitative PCR was performed on a iCycler iQ real-time PCR detection system (Bio-Rad, Hercules, Calif.) in a 20 μL reaction mix containing 4 μL RT product, reaction buffer (1×), dNTPs (200 μM/each), human GAPDH or LAMR primers (0.5 μM/each), 1U of Taq Polymerase (Fisher Scientific, Pittsburgh, Pa.), fluorescein (100 nM) and 1 μl of SYBR Green I (10,000× diluted to 1:75,000 v/v). Thermocycling was carried out over 40 cycles of 30 s at 95° C., 30 s at 60° C. and 1 min at 72° C. The sequences of the primers used were as follow:

hLAMR forward primer (on exon 2):
5'-CTCAAGAGGACCTGGGAGAAGC-3' (SEQ ID NO: 2)

hLAMR reverse primer (on exon 3):
5'-TGGCAGCAGCAAACTTCAGC-3' (SEQ ID NO: 3)

hGAPDH forward primer:
5'-CACCAGGGCTGCTTTTAACTCTGGTA-3' (SEQ ID NO: 4)

hGAPDH reverse primer:
5'-CCTTGACGGTGCCATGGAATTTGC-3' (SEQ ID NO: 5)

hGAPDH was chosen as the housekeeping gene for comparative analysis. The fold change in LAMR relative to the GAPDH endogenous control was determined by: fold change=$2^{-\Delta(\Delta C_T)}$, where $\Delta C_T = C_{T(LAMR)} - C_{T(GAPDH)}$, and $\Delta(\Delta C_T) = \Delta C_{T(ES-2/Fluc/\alpha LRP)} - \Delta C_{T(ES-2/Fluc)}$. $C_T$ is the threshold cycle determined at 84° C. for fluorescence data collection.

Results

Example 6

Figure 6A:
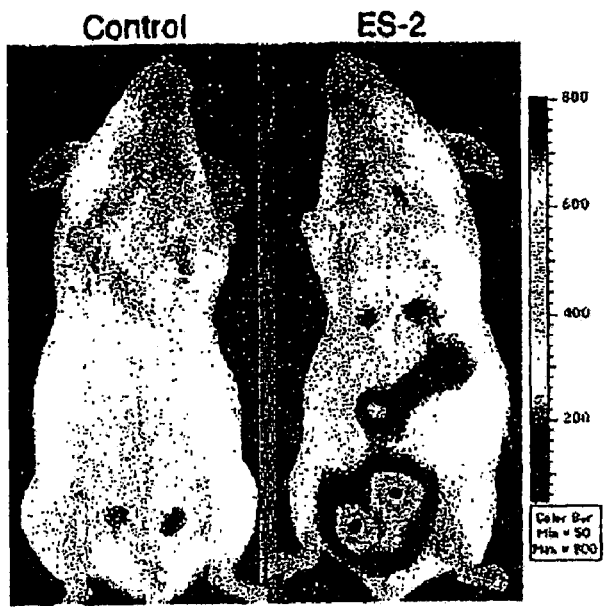
FIGS. 6(A-D) Sindbis vector specifically infects metastasized ES-2 cancer cells throughout the peritoneal cavity. A, SCID mice were inoculated with $2 \times 10^6$ ES-2 cells on day −5 and were i.p. treated with a single injection of Sindbis/Fluc vector on day 0. On the next day (day 1) the bioluminescence signals, resulting from vector infection of ES-2 cancer cells, were monitored using the IVIS® system (right panel). Low level of background vector infection was observed in the lower abdomen of tumor-free control mice (left panel). B, After the first whole body IVIS® imaging on day 1, the peritoneum was removed for another IVIS® imaging of the peritoneal cavity. Despite a low level of infection in the peritoneal fat tissue of tumor-free control mouse, specific tumor infection of Sindbis/Fluc vector was observed throughout the peritoneal cavity of ES-2 inoculated mouse upper panels). Some mice received a second i.p. injection of Sindbis/Fluc vector on day 2 and we IVIS® imaged the peritoneal cavities on day 3 (lower panels). The background infection in the fat tissue disappeared completely and no detectable signals were observed elsewhere in the peritoneal cavity of control mouse. In contrast, Sindbis/Fluc vector infection was sustained in the ES-2 tumor metastases. C, The organs in the double-treated ES-2 inoculated mouse (lower right panel in 2B) were harvested and imaged. Specific vector infection was exclusively observed in ES-2 metastases. The tumor metastases are shown in circles. Similar specific tumor targeting was also observed in ES-2 inoculated mice that received only a single Sindbis/Fluc treatment (data not shown). D, Corresponding tumor metastases (indicated by arrows) were observed microscopically at this early stage of disease progression in the omentum/pancreas, bowel, and peritoneum. Lung metastases four weeks after ES-2/Fluc inoculation were also observed. Bar: 500 μm.
Figure 6B:
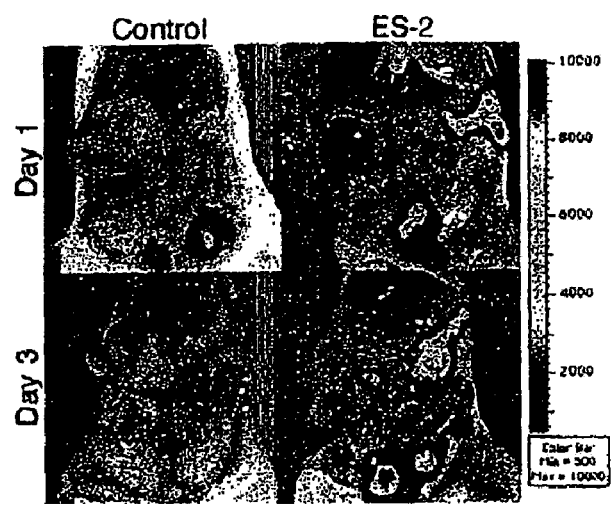

Sindbis Vectors Specifically Target ES-2 Metastases Throughout the Peritoneal Cavity I.p. injection (on day 0) of Sindbis/Fluc, which carries a Fluc gene, enabled the specific infection/detection of ES-2 metastases in SCID mice. In ES-2 inoculated mice, substantial vector infection was observed in regions corresponding to the pancreas/omentum, bowel and peritoneal fat (FIG. 6A, right panel). Low levels of Sindbis/Fluc infection were observed in the lower abdomen of some tumor-free control mice (FIG. 6A, left panel). Another set of IVIS® imaging as performed after the removal of the peritoneum to examine the exact location of vector infection in both control and ES-2 inoculated mice (FIG. 6B, day 1).

Figure 6C:
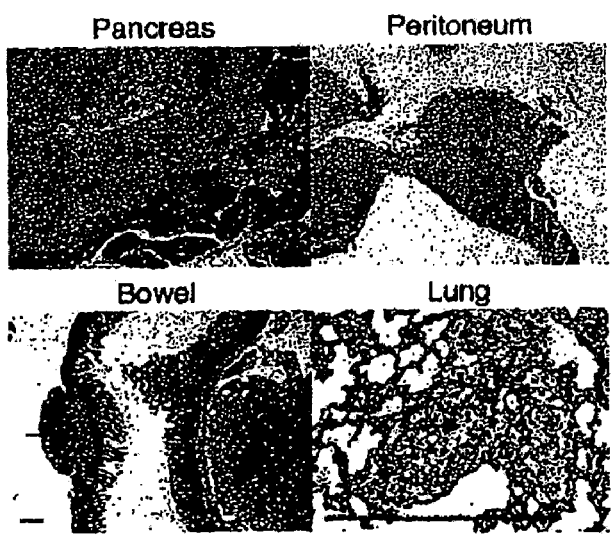

To determine if repeated administration of Sindbis vectors leads to accumulative infection in tumor-free mice, a second dose of Sindbis/Fluc vector was i.p. injected to both control and ES-2 inoculated mice on day 2 and performed IVIS® imaging on day 3. Interestingly, control mice that receive the second Sindbis/Fluc injection showed no detectable IVIS® signal in the peritoneal cavity while the vector infection signal in tumor metastases remained high in the ES-2 inoculated mice (FIG. 6B, day 3). The specific vector infection was histologically confirmed in tumor metastases in several tissues/organs, such as peritoneal fat, peritoneum, diaphragm, pancreas, and the bowel (FIG. 6C, organs harvested from same mouse (ES-2 day 3) in FIG. 6B). In tumor-free control mice, except for the transient background signals observed in the fatty tissue after the first treatment, no vector infection signal was detected in the peritoneal cavity. ES-2 inoculated mice that received only a single Sindbis/Fluc treatment on day 0 showed decreased bioluminescence signals in tumors on day 3 compared with those treated twice (data not shown). Increased bioluminescence signals in twice treated mice suggested that while a single vector treatment is capable of detecting widespread metastases in the peritoneal cavity, it is not sufficient to infect all tumor cells within the same metastatic implant. Successful Sindbis cancer therapy may require repetitive treatments in order to achieve good therapeutic effects.

Figure 6D:
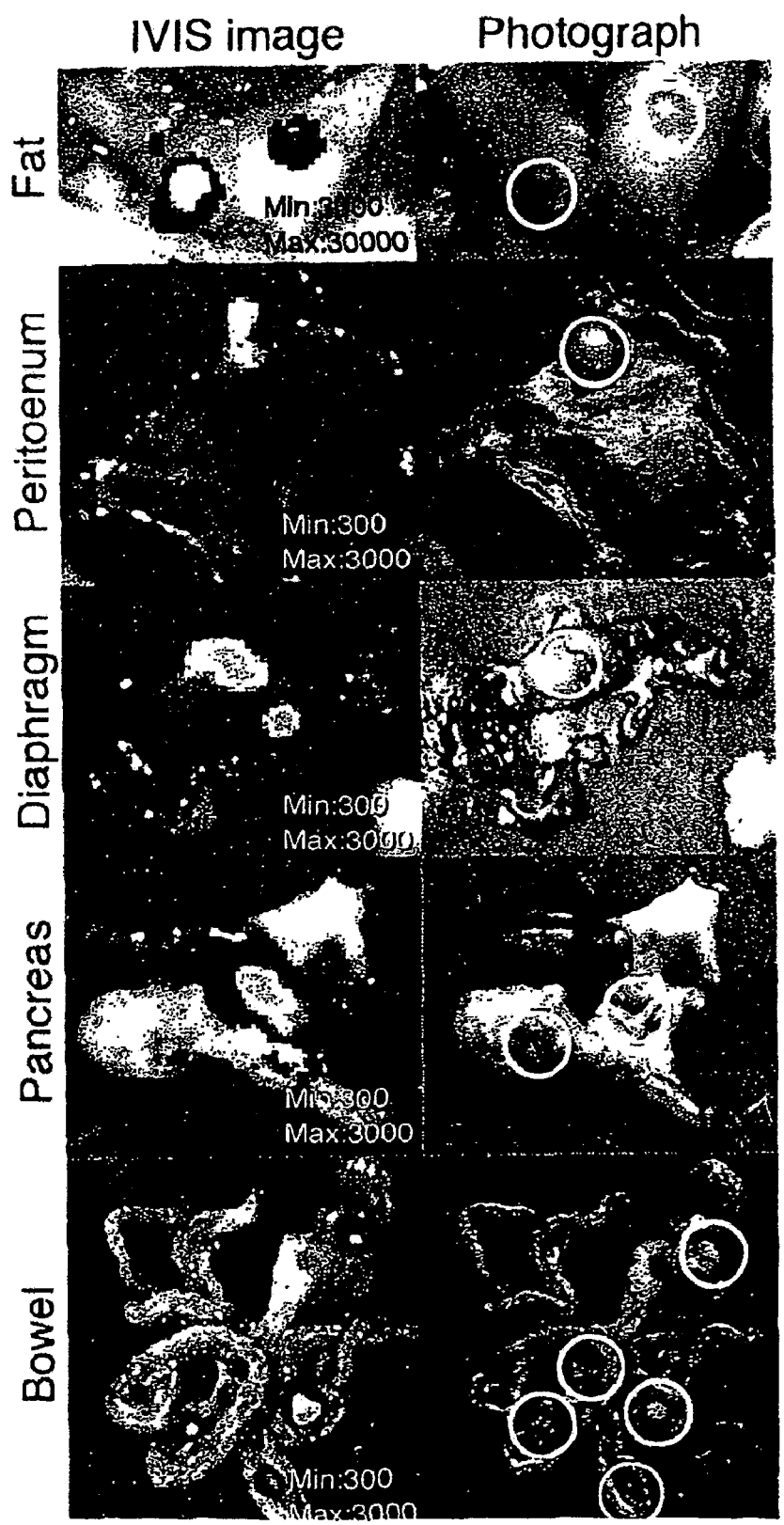

The presence of tumor metastases was histologically confirmed within several tissues of the peritoneal cavity at this early stage of disease progression, including pancreas, omentum, mesentery, and the peritoneum (FIG. 6D). Four weeks after tumor inoculation, lung micrometastases were also observed in ES-2 tumors (FIG. 6D). The lung metastases may be established via the lymphatic pathway since we observed the presence of tumor in the mediastinal lymph nodes of the chest (data not shown).

Figure 7:
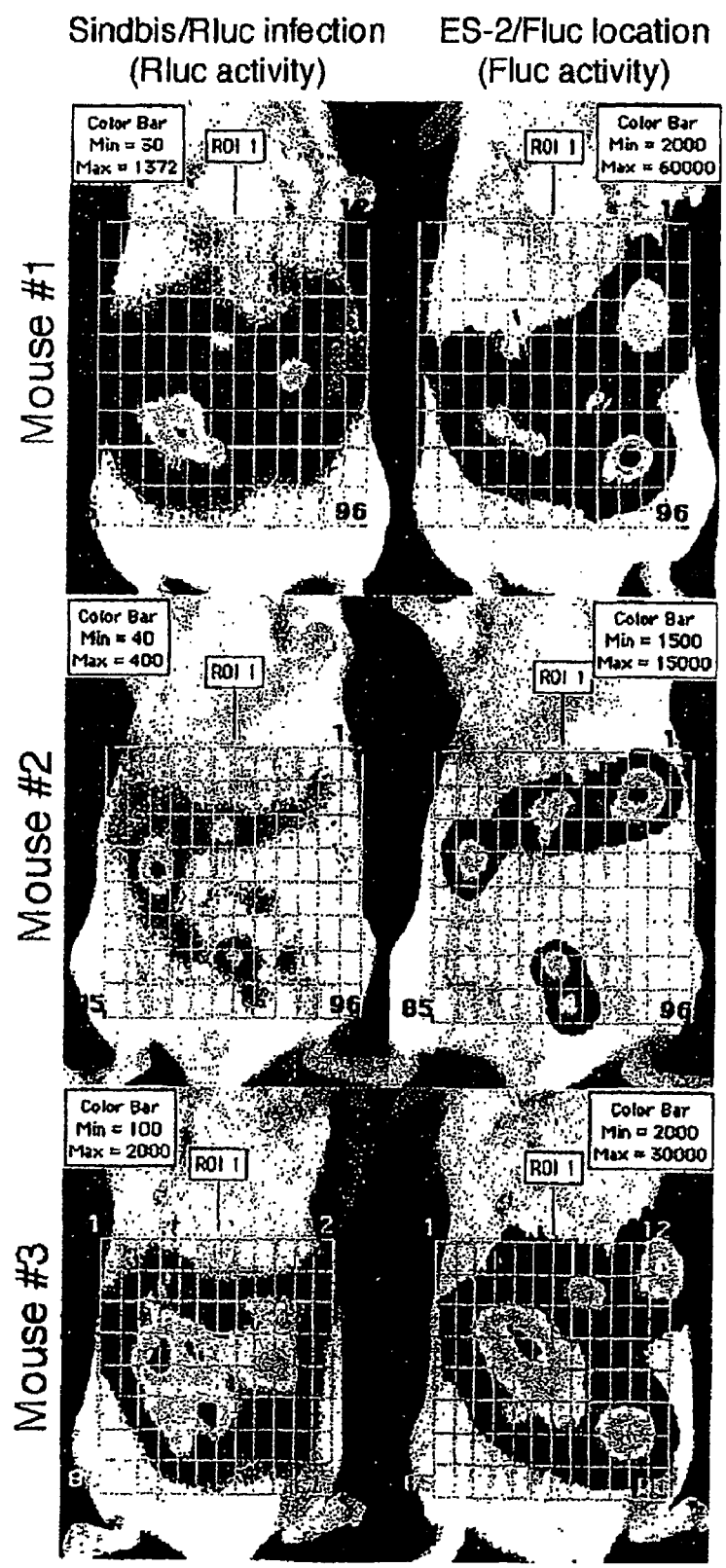
FIG. 7 Sindbis/Rluc infection co-localized with the metastasized ES-2/Fluc tumors in the peritoneal cavity as determined by the IVIS® system. SCID mice were i.p. inoculated with $1.5 \times 10^6$ ES-2/Fluc cells. Five days later while the disease was still microscopic, inoculated mice received a single i.p. treatment of Sindbis/Rluc vectors and were imaged the next day. The first IVIS® imaging was done by i.p. injection of Rluc substrate, coelenterazine, followed by a 5 min acquiring interval (left panel). 30 min after the coelenterazine injection, when the short-lived Rluc signals faded away, Fluc substrate, D-luciferin, was i.p. injected to determine the ES-2/Fluc tumor locations (right panel).

To establish the degree and specificity of Sindbis infection of tumor cells, imaging studies were conducted that measured independent bioluminescent signals from tumor cells and vectors. Since the ES-2/Fluc cells express the firefly luciferase gene, a Sindbis vector, Sindbis/Rluc was generated, which carries a different luciferase gene cloned from soft coral *Renilla renifomis* (Rluc) for IVIS® imaging. Firefly luciferase uses D-luciferin while *Renilla* luciferase uses coelenterazine to generate bioluminescence; the two luciferases are highly substrate specific and do not cross-react (19). By switching substrates, the Rluc (FIG. 7, left) and Fluc activities (FIG. 7, right) were separately determined in vivo using the IVIS® system. For quantitative analysis, the bioluminescence signals generated in the same animal from Sindbis/Rluc and ES-2/Fluc were quantitated using LIVING IMAGE® software. The images of Rluc and Fluc signals were grided (12×8=96 boxed regions) and corresponding regions were analyzed for statistical correlation. A highly significant correlation was established (P<0.0001). Thus, data analysis indicate that a single i.p. delivery of Sindbis vectors leads to efficient infection of the metastasized tumor cells throughout the peritoneal cavity.

Figure 8A:
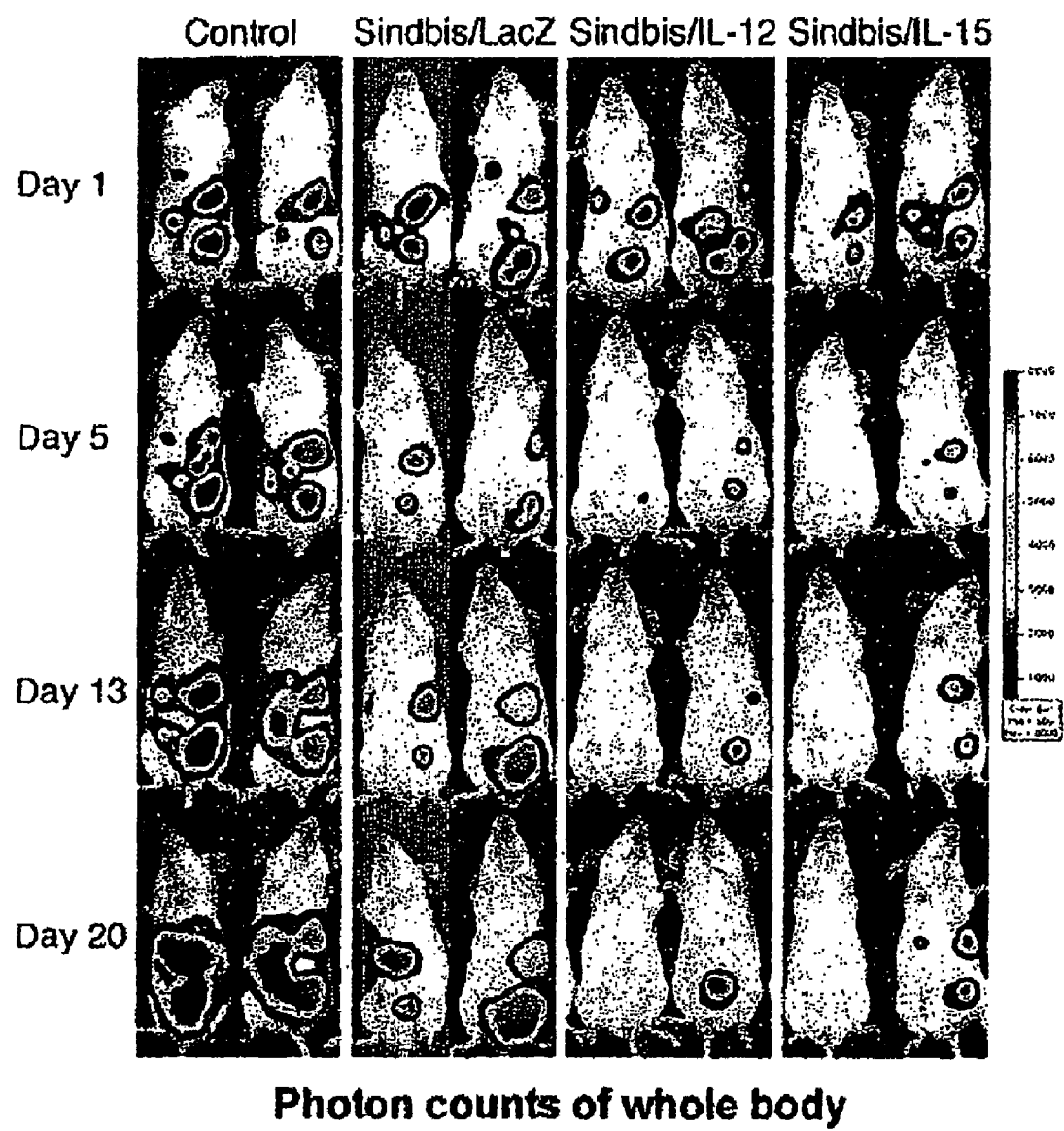
FIGS. 8(A and B) Sindbis vectors suppress disease progress in mice inoculated with ES-2/Fluc cells. A, $1.5 \times 10^6$ ES-2/Fluc cells were i.p. inoculated into SCID mice on day 0. Next day (day 1), mice were imaged using the IVIS® Imaging System using D-luciferin as substrate and were split into four groups: control (n=12), that received no vector treatment and Sinbis/LacZ (n=9), Sindbis/IL-12 (n=5) and Sindbis/IL-15 (n=4) groups that received daily i.p. treatments of corresponding Sindbis vectors. All Sindbis treatments suppressed the tumor growth on the mesentery and diaphragm, and reduced the signals on the omentum compared with control mice. The signals by the left legs at the lower abdomens were intramuscular tumors at tumor inoculation sites. B, Quantitative analysis of the whole body total photon counts of control and Sindbis treated mice. Error bars represent the s.e.m.
Figure 8B:
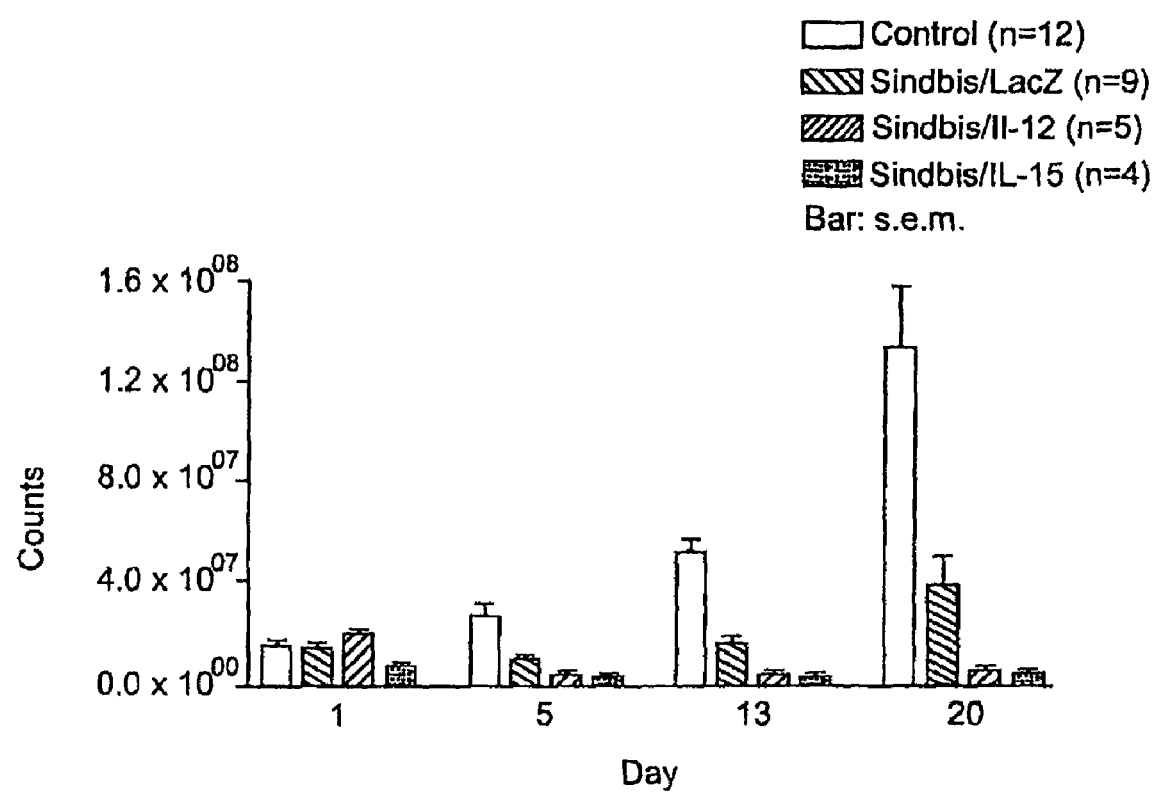

It is known that Sindbis virus induces cytopathic effects in infected mammalian cells, which results from its ability to induce apoptosis (4-7). Increased caspase-3 activity was observed within ES-2 cells after Sindbis infection (data not shown). Therefore, the efficacy of Sindbis vectors carrying different gene payloads against metastatic ovarian cancer in ES-2/Fluc models was compared. Three different vectors were tested: Sindbis/LacZ, which carries the bacterial β-galactosidase gene; Sindbis/IL-12, which carries mouse IL-12 genes; and Sindbis/IL-15, which carries a mouse IL-15 gene. IL-12 and IL-15 are known to elicit anti-tumor activity by activation of natural killer (NK) cells (20, 21). On day 0, all SCID mice were i.p. inoculated with 1.5×10$^6$ ES-2 cells and daily treatments were started on day 1. Control mice did not receive vector treatment. Total whole body photon counts were determined by IVIS® imaging on day 1, 5, 13, and 20 to determine disease progression of ES-2/Fluc metastases (FIG. 8A) (3). Without any anti-tumor cytokine gene, the Sindbis/LacZ vector significantly suppressed disease progression compared with untreated control mice (FIG. 8B, two-way ANOVA: P<0.0001). The IL-12 and IL-15 cytokine genes further enhanced the anti-tumor activity of Sindbis vectors compared with mice treated with Sindbis/LacZ (FIG. 8B, two-way ANOVA: P=0.0081 for Sindbis/IL-12 and P=0.0026 for Sindbis/IL-15). Within 5 days, the Sindbis/IL-12 treatments reduced the tumor load by, on average, more than 11 fold to ~140,000 tumor cells (FIG. 8B). This signifies a reduction of greater than 95% when compared to untreated mice, while, the increase in photon counts indicated that the number of cells by day 5 had increased, on average, 1.9 fold to ~3×10$^6$ tumor cells. These results suggest that, in addition to specific infection/detection, repeated vector treatments suppress tumor growth likely via induction of apoptosis. Furthermore, incorporation of anti-tumor genes into this vector system further enhances the efficacy against tumors.

Example 7

Figure 9A:
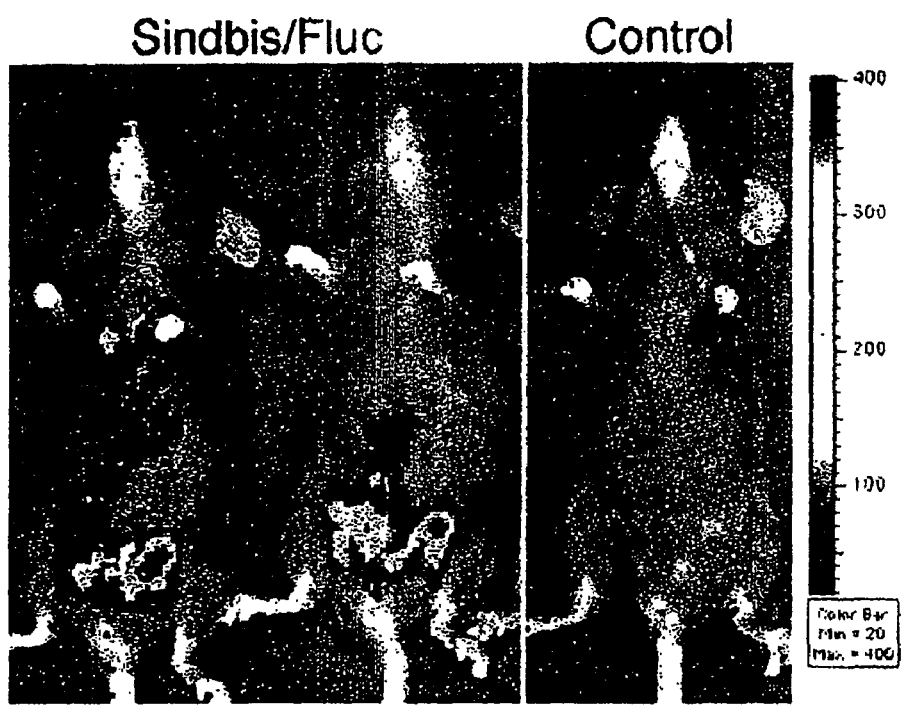
FIGS. 9(A-D) Sindbis/Fluc vectors are capable of specific detection of syngenic MOSEC metastases in the peritoneal cavity of immunocompetent C57BL/6 mice. A, Four weeks after i.p. inoculation with $1 \times 10^7$ MOSEC cells, mice were treated with a single i.p. injection of Sindbis/Fluc vectors and were IVIS® imaged the next day. Tumor-free control mice were treated with Sindbis/Fluc and imaged in parallel. Substantial bioluminescent signals were observed in the peritoneal cavities of MOSEC-inoculated mice but not in the ones of control mice. B, In order to visualize the specific tumor infection, a single i.p. injection of Sindbis/Fluc vector was administered to C57BL/6 mice bearing MOSEC tumors for 7 weeks. By then the mice showed the onset of ascites development and had severe carcinomatosis that was directly visible during necropsy. The left panel shows the whole body imaging the day after a single i.p. Sindbis/Fluc treatment and the right panels show imaging of the peritoneal cavity of the same animal. The tumor metastases are shown in circles. C, The imaging of the organ array indicated that Sindbis/Fluc vector specifically infects MOSEC metastases on the peritoneum (1), bowel/mesentery (2), small and great omentum (4), next to stomach and spleen, liver surface (5), kidney (6), peritoneal fat (7), diaphragm (8), and uterus (9). No substantial signals were observed in the heart (3), lung (3) and brain (10). Circles indicate the MOSEC metastases locations visible with regular light photography. D, Microscopically, H&E staining confirmed the presence of MOSEC tumors (indicated by arrows) on the pancreas, peritoneal fat, mesentery, and diaphragm. Bar: 250 □m.
Figure 9B:
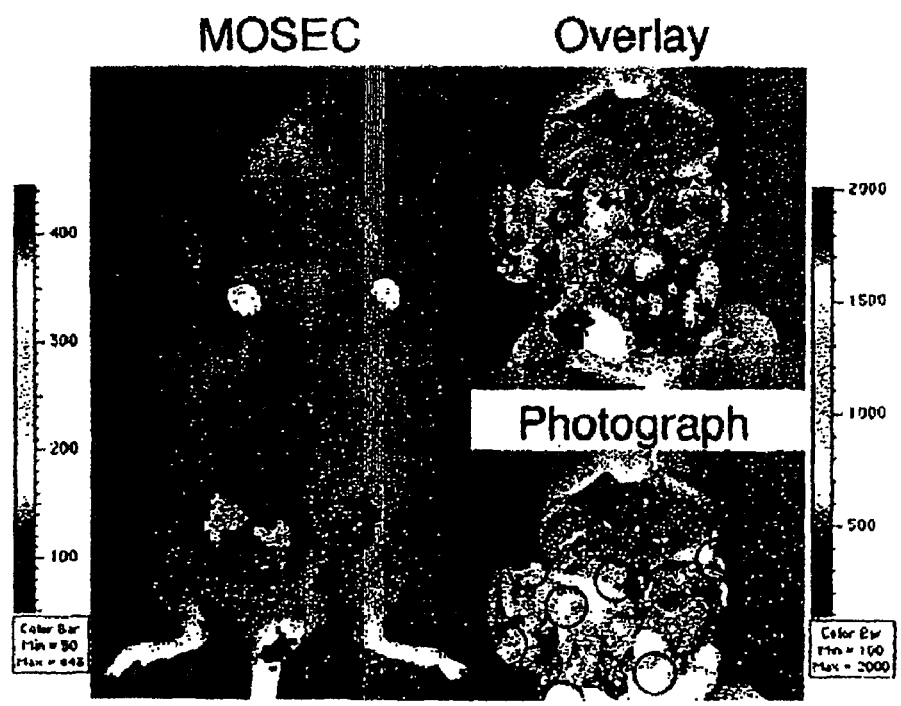
Figure 9C:
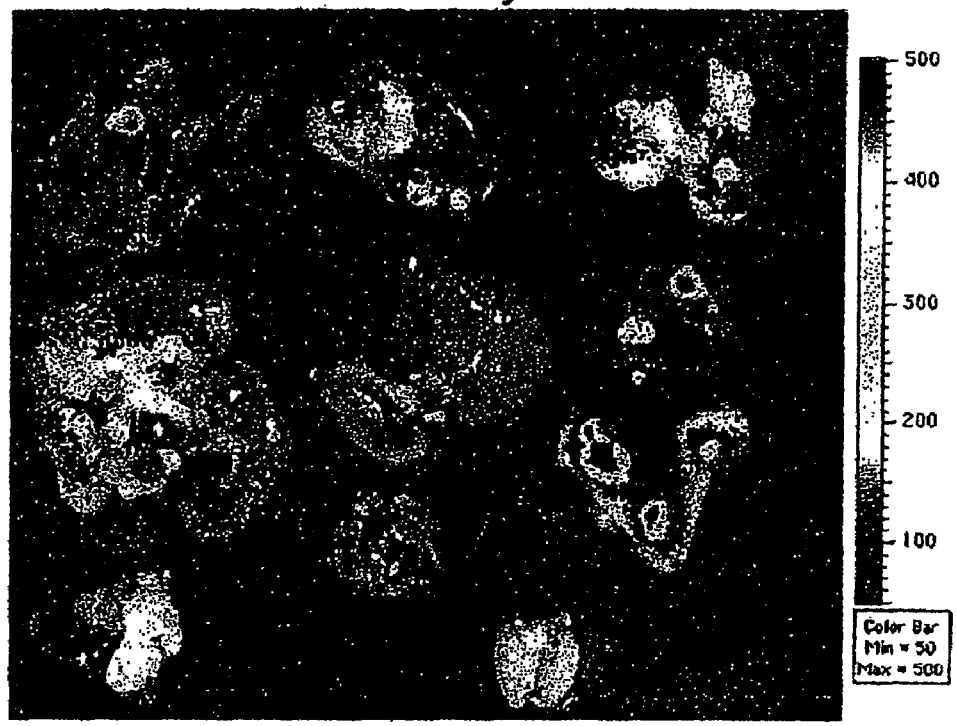
Figure 9C:
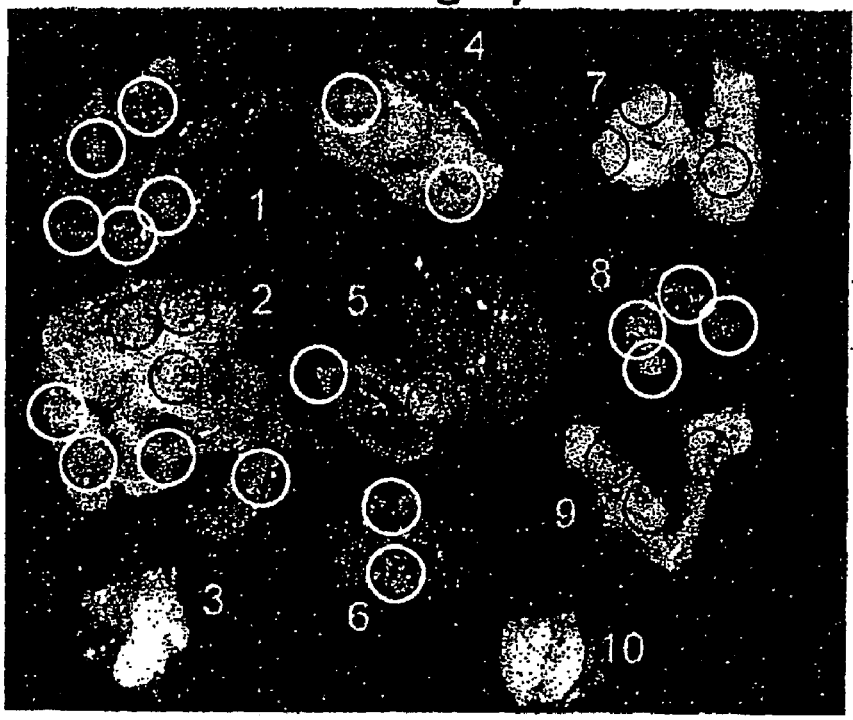
Figure 9D:
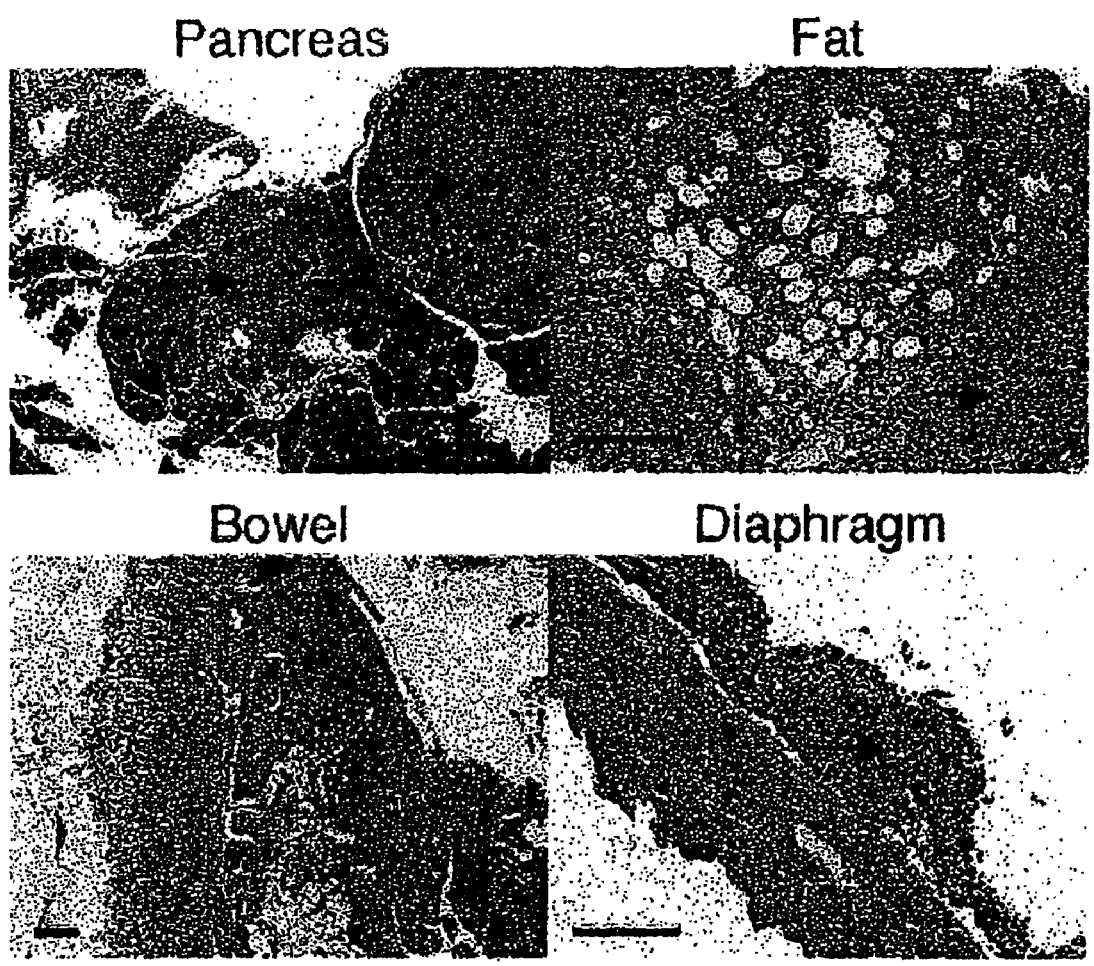

Sindbis Vectors Specifically Target Mouse MOSEC Ovarian Cancer Metastases in a Syngenic Animal Model The advanced ovarian cancer model described above was established by inoculation of human ES-2 cells into SCID mice that rapidly developed advanced disease. In this model, the possibility that the tumor specific infection results from a preferential tropism of Sindbis vectors for human cells could not be rule out. Further, as SCID mice lack intact immune systems, this model does not assess the impact of potential immune responses on delivery and targeting of Sindbis vectors to tumor cells. A previously established syngenic ovarian cancer model in C57BL/6 immunocompetent mice (18) was used. I.p. inoculation of MOSEC cells into C57BL/6 induces a disease similar to that induced by i.p. injection of ES-2 cells into SCID mice, albeit the MOSEC cells grow more slowly in animals. Four weeks after i.p. MOSEC inoculation, the mice received a single i.p. treatment of Sindbis/Fluc. Tumor-free control mice also received Sindbis/Fluc treatment. As had been the case in the ES-2/Fluc SCID model, substantial bioluminescent signals indicating widespread metastasis in the peritoneal cavity of tumor-inoculated mice was observed (FIG. 9A). No significant bioluminescent signals were generally observed, although low background signals in the peritoneal fat were observed, sometimes in control mice. In order to visualize the specific infection in tumor metastases, a C57BU/6 mouse bearing MOSEC tumors for 7 weeks was used. At this later time point, ascites were visible (FIG. 9B, left panel) and extensive tumor metastases were visually observed during autopsy (FIG. 9B, lower right panel). When given a single i.p. injection of Sindbis/Fluc vectors, the whole body imaging revealed a weaker bioluminescent signal than mice treated four weeks after tumor inoculation. This probably results from the development of severe ascites which decreases the excitation and subsequent detection of luminescent signals and that vector dosage must infect a much larger area and is thus less concentrated. Sindbis/Fluc vector demonstrated specific targeting to most of the MOSEC metastases within the peritoneal cavity (FIG. 9B, upper right panel). In addition, the vector could efficiently infect metastases in several tissues, similar to the ES-2 model (FIG. 9C). Tumor metastases were confirmed histologically on these tissues (FIG. 9D).

Figure 10A:
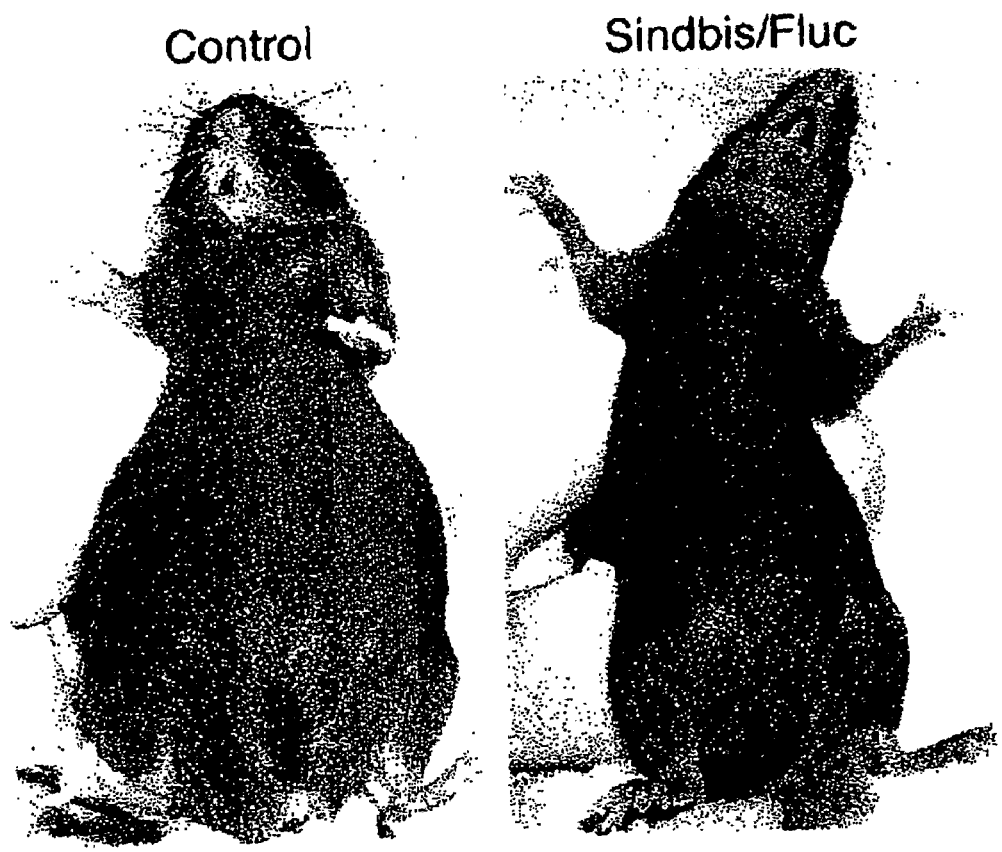
FIGS. 10(A and B) Sindbis vector treatments suppress disease progression of C57BL/6 mice i.p. inoculated with MOSEC cancer cells. Mice were i.p. inoculated with $1 \times 10^7$ MOSEC cells on day 0 and the daily i.p. treatments of Sindbis/Fluc vector started on day 34. Control mice received no Sindbis treatment. A, On day 47, 5/7 control mice have severe ascites compared to only ⅛ in Sindbis/Fluc mice whose ascites was much less intense. B, The survival curves of different treatment group. Sindbis/Fluc significantly prolonged the survival of mice carrying MOSEC cancer (Sindbis/Fluc v.s. control:P<0.0071, log rank test).
Figure 10B:
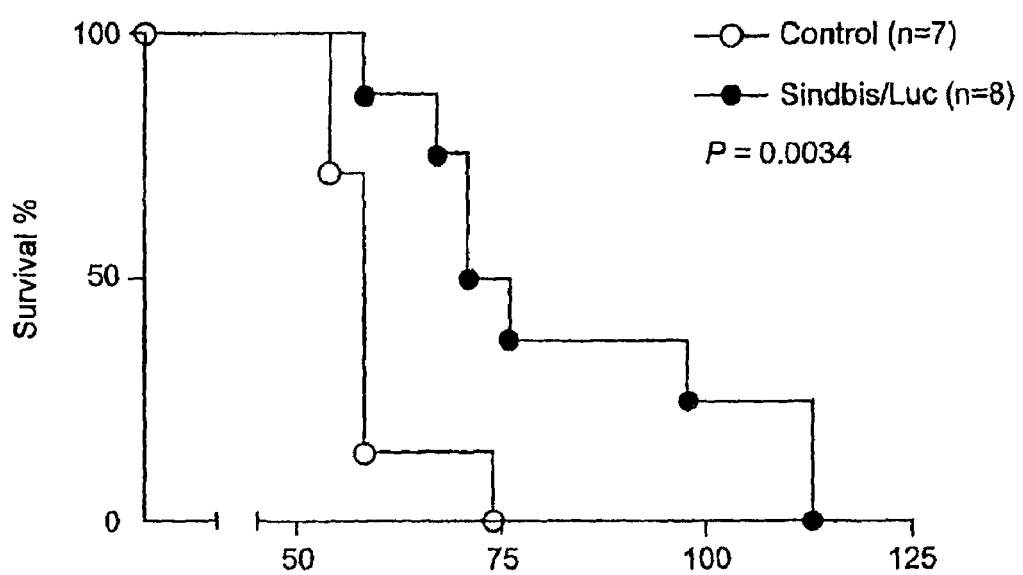

In addition to specific detection, Sindbis vectors suppressed disease progression. Mice treated with Sindbis/Fluc have lower incidence of ascites after two weeks of treatments (7 weeks after tumor inoculation). By then, 5/7 untreated control mice developed severe ascites compared to only 1/8 in Sindbis/Fluc mice (FIG. 10A). In addition, the treated mouse with ascites was considerably less sick. Disease suppression was also reflected in significant prolongation of survival in Sindbis-treated mice (FIG. 10B).

Example 8

LAMR Expression Levels Correlate with the Infectivity of Sindbis Vectors

Figure 11A:
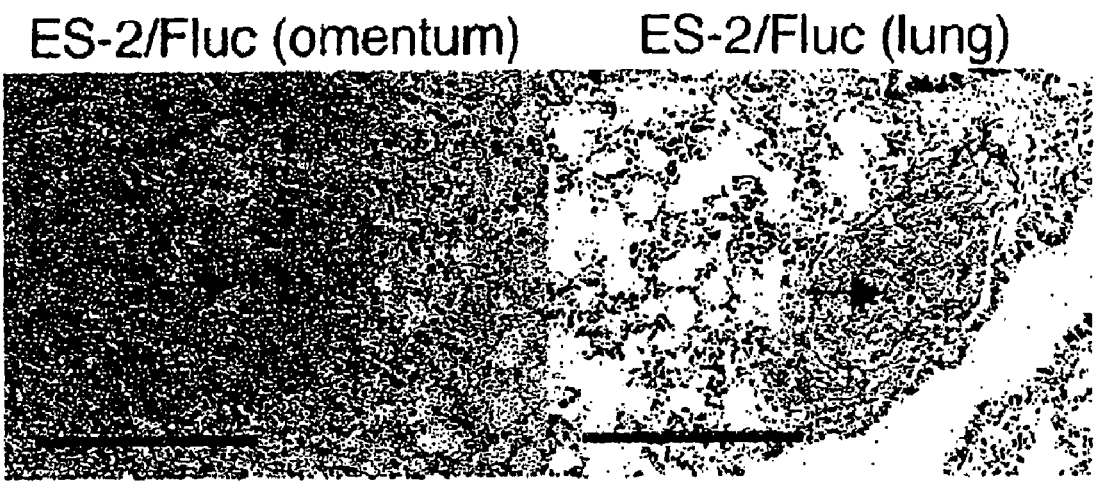
FIGS. 11(A-C) Infectivity of Sindbis vectors correlated with the expression of LAMR. A, Immunohistochemical staining on tumor sections with an antibody spcific to the laminin receptor precursor (LRP) of LAMR revealed that tumor metastases (indicated by arrows) over-express LAMR in both ES-2/Fluc and MOSEC models. Similarly, high leves of LAMR expression in spontaneous tumors in MSV-RGR/p15$^{+/-}$ transgenic mice were also observed, which were successfully targeted by Sindbis vectors as demonstrated previously (3). Bar: 250 μm. B, ES-2/Fluc/αLRP cells, that stably expresses a siRNA specifically against LRP messenger, had a lower expression level of LAMR as indicated by real-time RT-PCR assay. A pair of primers specific to human GAPDH mRNA was also included to provide an internal control. The graph represents the average of three independent assays using 1000, 500, 250 ng of total RNA, and the error bar indicates the standard error of the means (s.e.m.). C, To determine the Sindbis infectivity of these two cell lines, ES-2/Fluc and ES-2/Fluc/LRP cells were infected with Sindbis/LacZ vectors at MOI of 100, 10, and 1.

LAMR has been identified as the cell surface receptor for Sindbis infection to mammalian cells (8, 9). To establish whether this is consistent with the hypothesis that Sindbis vectors preferentially infect tumor vs. normal cells due to differences in LAMR expression, immunohistochemical staining on tumor sections with an antibody specific to the laminin receptor precursor (LRP) was performed. The ES-2/Fluc tumors express higher levels of LAMR than normal tissues (FIG. 11A). Similarly, higher levels of LAMR expression in MOSEC metastases and spontaneous tumors in MSV-RGR/p15$^{+/-}$ transgenic mice (FIG. 11A) was observed, which are also targeted by Sindbis vectors (3).

Figure 11B:
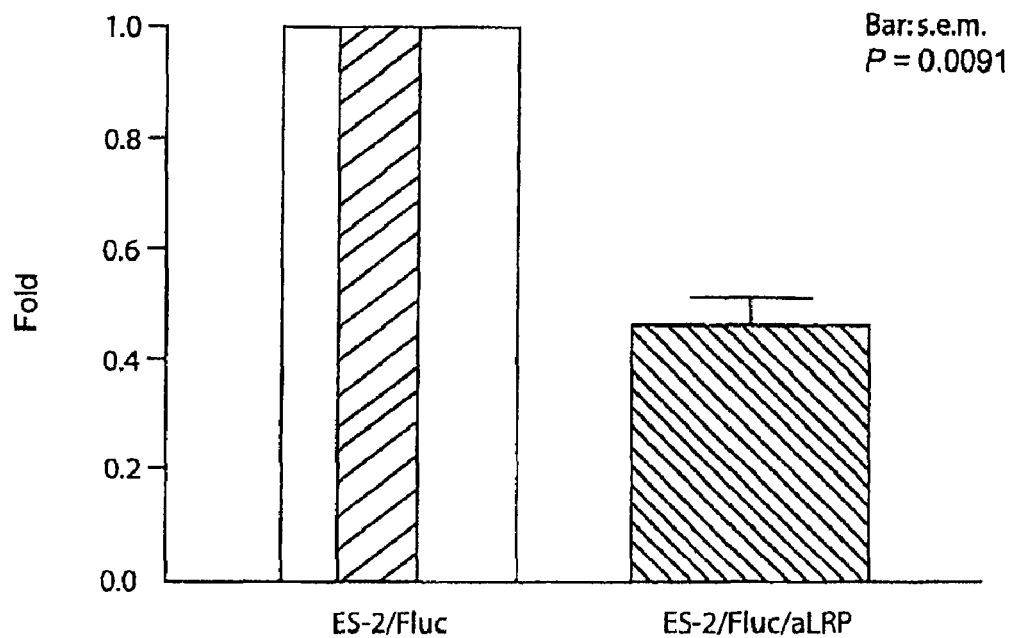
Figure 11C:
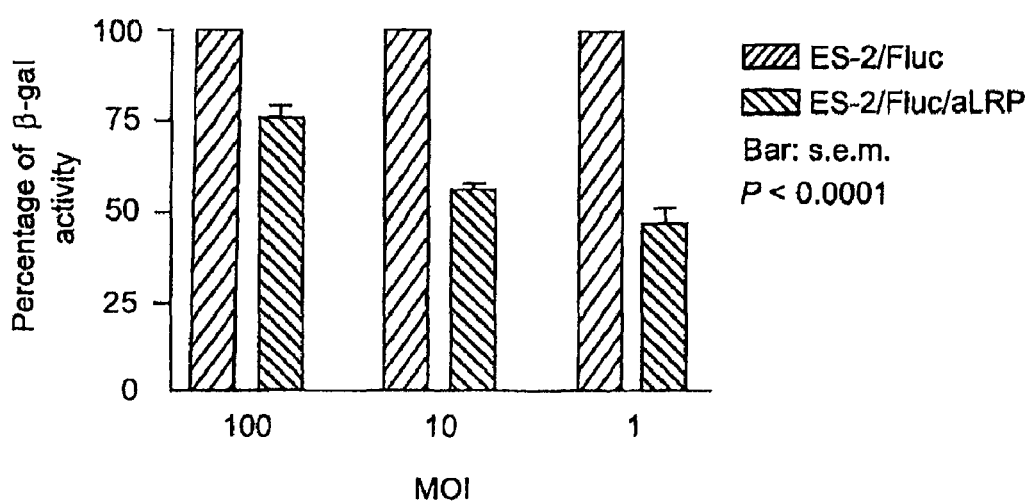

To further investigate the correlation between LAMR expression and Sindbis vector infection, an ES-2 derived cell line, ES-2/Fluc/αLRP, that stably expresses a siRNA specifically against LRP messenger in addition to the plasmid backbone for Fluc expression as in ES-2/Fluc cells was generated. Real-time RT-PCR was performed to determine the expression levels of LAMR in ES-2/Fluc and ES-2/Fluc/αLRP cells. A pair of primers specific to human GAPDH mRNA was included to serve as an internal control. The results indicate that the LAMR expression level in ES-2/Fluc/αLRP cells is about 40% compared with ES-2/Fluc cells (FIG. 11B). To determine the Sindbis infectivity of these two cell lines, ES-2/Fluc and ES-2/Fluc/αLRP cells were infected with Sindbis/LacZ vectors at MOI of 100, 10, and 1. As hypothesized, ES-2/Fluc/αLRP cells that express less LAMR are infected less well by Sindbis vectors compared with ES-2/Fluc (FIG. 11C). These data indicate that the Sindbis infectivity of ES-2 cells correlates with the expression levels of LAMR and are concordant with previously reports that indicated LAMR as the mammalian receptor for Sindbis infection (8, 9).

Discussion

In Examples 6-11 above, the capability of Sindbis viral vectors to specifically infect and detect micro and macro tumor metastases in the peritoneal cavity was demonstrated. The advantage of Sindbis viral gene therapy vectors for tumor detection is that the vector can markedly amplify the signals by over-expression of the transgene markers. While luciferase expression may not be suitable for imaging of tumor cells in humans, because of the potential greater depths at which such cells might be found in humans versus mice, other more tissue penetrating reporter genes, such as the herpes simplex virus type-I thymidine kinase (HSV1-tk) and dopamine-2 receptor ($D_2R$) genes, can be incorporated into Sindbis vectors for tumor detection using positron emission topography (PET) (22).

In order to specifically detect tumor cells, viral vector systems require either tumor specific receptors for infection or, alternatively, the use of tumor specific promoters for reporter transgene expression in tumor cells. In general, vectors using tumor-specific promoters for gene activation are taken up and expressed by only a small proportion of the targeted tumor cells. In contrast, because vectors based on Sindbis virus infect via a ubiquitously expressed receptor that is differentially expressed between tumor and normal cells, these vectors achieve efficient tumor targeting and robust transgene expression using the viral promoter. Sindbis vectors rapidly and extensively amplify transgenes once they infect target cells. Sindbis vectors thus provide faster and more sensitive detection of tumor cells via systemic administration. In addition, the imaging data, along with previous biochemical analysis of transgenes expression (2), indicates that no Sindbis vector infection of liver or other organs occurs in mice upon systemic delivery, permitting the use of relatively high doses of Sindbis vectors capable of suppressing metastatic tumor growth.

The cell surface receptor for Sindbis has been identified as the high affinity LAMR (8), a glycosylated membrane protein that mediates cellular interactions with the extracellular matrix, and it is over-expressed and unoccupied (compared to normal cells) in the vast majority of tumors (23-26). Several reports suggest that higher levels of LAMR on human tumor cells provide growth advantages such as more aggressive invasiveness and metastatic spread (10-14). This fortuitous event also provides a differential marker on the surface of normal and tumor cells for Sindbis attachment and infection.

LAMR is an attractive target on ovarian cancer cells since they have been shown to express high levels of this receptor (15-17). In the advanced ovarian cancer models, both ES-2/Fluc and MOSEC cells express higher levels of LAMR than normal tissues (FIG. 11A) and can be specifically infected by Sindbis vectors (FIGS. 6 and 10). Similar higher expression levels of LAMR were also observed in spontaneous tumors of MSV-RGR/p15$^{+/-}$ transgenic mice, which were also targeted by Sindbis vectors (3). In the peritoneal cavity, it is likely that most of the LAMRs on the tumor cells in the ascetic fluid are not occupied by the ligand laminin, and therefore serve as ideal targets for Sindbis vector infection. The observation that Sindbis treatments suppressed ascites formation in this study supports this point of view.

Although the exact composition of LAMR is still unknown, one essential component of the LAMR has been identified as a 37-kDa laminin receptor precursor (LRP) (27). It is believed that LRP is modified post-translationally and forms heterodimers (28) with other glycosylated proteins prior to translocation to the cell surface. One of its likely partners is heparan-sulfated proteoglycan (HSPG) (29). It is relevant to note that a number of laboratories have also identified the LAMR as the target for prion protein (29-34). For example, Hundt et al. (29) have shown that the prion protein binds to two sites of this LAMR. One of the binding sites is dependent for optimal binding in the presence of a heparan sulfate arm of a HSPG molecule, but the other binding site appears to function independently of heparan sulfate.

It has been proposed that heparan sulfate plays a role in the attachment of Sindbis vectors to cells (35). However, while the interaction with heparan sulfate enhances the infection efficiency, it is not required for infection (35). Therefore, it is possible that the Sindbis vectors infect tumor cells via interactions with both LRP and heparan sulfate.

The data presented herein indicate that the tumor specificity of Sindbis vectors is not likely to be due to a different tropism between human and mouse cells. The vector is as capable of specific infection/detection of murine MOSEC ovarian cancer cells (FIG. 9) as it is of human ES-2/Fluc cells in SCID mice (FIG. 6). In addition, Sindbis vectors can specifically infect spontaneous tumors in MSV-RGR/p15$^{+/-}$ transgenic mice (3). Since no human cells are involved in the latter model, the specific infection of Sindbis vector is likely due to fundamental differences between normal and tumor cells such as expression levels of LAMR.

Infection of Sindbis vector induces apoptosis without any cytotoxic transgene in vitro (4-7) and in vivo (2). Despite the cytotoxicity to infected cells, systemic delivery of Sindbis vectors shows no observable morbidity in experimental animals.

In most cases, after wild type replication-capable Sindbis virus enters the bloodstream, virus titers reach high levels throughout all organs (36, 37). Yet, minimal, self-limiting disease (usually no more than one week in duration and accompanied only by mild symptomology) is associated with the wild-type virus (36, 37). While maintaining the capability of reaching all organs through the bloodstream, it has been shown that the laboratory strain of Sindbis used to produce all of the vectors does not cause any disease or adverse consequences in humans (36, 37). One reason for this is that all of the vectors that were used are replication defective. That is, once these vectors infect cells they cannot propagate to other cells. While they are able to infect virtually all target cells, the fact that they do not replicate and do not integrate makes them very safe.

In tumor-free mice, only very low levels of vector infection in the peritoneal fat after the initial i.p. vector treatment were observed (FIG. 7A). For reasons that require further investigation, this low level infection resolved after a subsequent vector treatment (FIG. 7B). That is, no infection is detectable in normal mice after the second injection of Sindbis vectors. In contrast, specific tumor infection persists during the course of treatments. Since these phenomena occur in SCID mice, which are immunodeficient, the loss of vector infection in normal fat tissues may be due to other innate anti-viral responses, such as type I interferon (IFN-I) production, which protect surrounding normal tissues from secondary vector infection. Several studies suggest that, during oncogenesis, tumor cells evolve to be less responsive to interferon stimuli compared with normal cells (38). Therefore, it is plausible that after the initial vector infection IFN-I production is induced, protecting the normal fat tissue from secondary infection. On the other hand, tumors, which often demonstrate defects in IFN-I response, are still subject to secondary Sindbis vector infection and eventually succumb to the vector cytotoxicity. In this aspect, the difference in the responsiveness of IFN-I may provide Sindbis vectors another level of specificity for tumor cells.

All of the present studies were done with replication-defective vectors. It is plausible to argue that use of a replication-capable vector system could enhance the anti-tumor effects. However, without wishing to be bound by theory, it is believed that this will not be necessary with Sindbis vectors. Rather, additional studies or combination of Sindbis vectors with other agents may allow development of protocols that can achieve complete eradication of ovarian tumor cells. Sindbis vectors have a decisive safety advantage over replication competent viruses for use in gene therapy.

In conclusion, it has been shown, in an aggressive mouse ovarian cancer models, that Sindbis vectors can achieve two major therapeutic goals of cancer gene therapy: specific detection of tumor cells, primary and metastatic, and efficient tumor suppression.

REFERENCES FOR EXAMPLES 6-11

1. Fishman D A, Bozorgi K. The scientific basis of early detection of epithelial ovarian cancer: The national ovarian cancer early detection program (NOCEDP). In: Stack M S, Fishman DA, editors. Ovarian cancer. Norwell: Kluwer Academic Publishers; 2002. p. 3-28.
2. Tseng J C, Levin B, Hirano T, Yee H, Pampeno C, Meruelo D. In vivo antitumor activity of sindbis viral vectors. J Natl Cancer Inst. 2002; 94(23): 1790-802.
3. Tseng J C, Levin B, Hurtado A, et al. Systemic tumor targeting and killing by Sindbis viral vectors. Nat Biotechnol. 2004; 22(1): 70-7.
4. Levine B, Huang Q, Isaacs J T, Reed J C, Griffin D E, Hardwick J M. Conversion of lytic to persistent alphavirus infection by the bcl-2 cellular oncogene. Nature. 1993; 361(6414): 739-42.
5. Jan J T, Chattedjee S, Griffin D E. Sindbis virus entry into cells triggers apoptosis by activating sphingomyelinase, leading to the release of ceramide. J. Virol. 2000; 74(14): 6425-32.
6. Jan J T, Griffin D E. Induction of apoptosis by Sindbis virus occurs at cell entry and does not require virus replication. J. Virol. 1999; 73(12): 10296-302.
7. Balachandran S, Roberts P C, Kipperman T, et al. Alpha/beta interferons potentiate virus-induced apoptosis through activation of the FADD/Caspase-8 death signaling pathway. J. Virol. 2000; 74(3): 1513-23.
8. Wang K S, Kuhn R J, Strauss E G, Ou S, Strauss J H. High-affinity laminin receptor is a receptor for Sindbis virus in mammalian cells. J. Virol. 1992; 66(8): 4992-5001.
9. Strauss J H, Wang K S, Schmaljohn A L, Kuhn R J, Strauss E G. Host-cell receptors for Sindbis virus. Arch Virol Suppl. 1994; 9: 473-84.
10. Martignone S, Menard S, Bufalino R, et al. Prognostic significance of the 67-kilodalton laminin receptor expression in human breast carcinomas. J Natl Cancer Inst. 1993; 85(5): 398-402.
11. Sanjuan X, Fernandez P L, Miquel R, et al. Overexpression of the 67-kD laminin receptor correlates with tumour progression in human colorectal carcinoma. J Pathol. 1996; 179(4): 376-80.
12. de Manzoni G, Verlato G, Tomezzoli A, et al. Study on Ki-67 immunoreactivity as a prognostic indicator in patients with advanced gastric cancer. Jpn J Clin Oncol. 1998; 28(9): 534-7.

13. Taraboletti G, Belotti D, Giavazzi R, Sobel M E, Castronovo V. Enhancement of metastatic potential of murine and human melanoma cells by laminin receptor peptide G: attachment of cancer cells to subendothelial matrix as a pathway for hematogenous metastasis. J Natl Cancer Inst. 1993; 85(3): 235-40.
14. Ozaki I, Yamamoto K, Mizuta T, et al. Differential expression of laminin receptors in human hepatocellular carcinoma. Gut. 1998; 43(6): 837-42.
15. van den Brule F A, Castronovo V, Menard S, et al. Expression of the 67 kD laminin receptor in human ovarian carcinomas as defined by a monoclonal antibody, MLuC5. Eur J Cancer. 1996; 32A(9): 1598-602.
16. van den Brule F A, Berchuck A, Bast R C, et al. Differential expression of the 67-kD laminin receptor and 31-kD human laminin-binding protein in human ovarian carcinomas. Eur J Cancer. 1994; 30A(8): 1096-9.
17. Liebman J M, Burbelo P D, Yamada Y, Fridman R, Kleinman H K. Altered expression of basement-membrane components and collagenases in ascitic xenografts of OVCAR-3 ovarian cancer cells. Int J Cancer. 1993; 55(1): 102-9.
18. Roby K F, Taylor C C, Sweetwood J P, et al. Development of a syngeneic mouse model for events related to ovarian cancer. Carcinogenesis. 2000; 21(4): 585-91.
19. Bhaumik S, Gambhir S S. Optical imaging of *Renilla* luciferase reporter gene expression in living mice. Proc Natl Acad Sci USA. 2002; 99(1): 377-82.
20. Perussia B, Chan S H, D'Andrea A, et al. Natural killer (NK) cell stimulatory factor or L-12 has differential effects on the proliferation of TCR-alpha beta+, TCR-gamma delta+T lymphocytes, and NK cells. J. Immunol. 1992; 149(11): 3495-502.
21. Evans R, Fuller J A, Christianson G, Krupke D M, Troutt A B. IL-15 mediates anti-tumor effects after cyclophosphamide injection of tumor-bearing mice and enhances adoptive immunotherapy: the potential role of NK cell subpopulations. Cell Immunol. 1997; 179(1): 66-73.
22. Yaghoubi S S, Wu L, Liang Q, et al. Direct correlation between positron emission tomographic images of two reporter genes delivered by two distinct adenoviral vectors. Gene Ther. 2001; 8(14): 1072-80.
23. Liotta L A, Horan Hand P, Rao C N, Bryant G, Barsky S H, Schlom J. Monoclonal antibodies to the human laminin receptor recognize structurally distinct sites. Exp Cell Res. 1985; 156(1): 117-26.
24. Barsky S H, Rao C N, Hyams D, Liotta L A. Characterization of a laminin receptor from human breast carcinoma tissue. Breast Cancer Res Treat. 1984; 4(3): 181-8.
25. Terranova V P, Rao C N, Kalebic T, Margulies I M, Liotta L A. Laminin receptor on human breast carcinoma cells. Proc Natl Acad Sci USA. 1983; 80(2): 444-8.
26. Liotta L A, Rao N C, Barsky S H, Bryant G. The laminin receptor and basement membrane dissolution: role in tumour metastasis. Ciba Found Symp. 1984; 108: 146-62.
27. Rao C N, Castronovo V, Schmitt M C, et al. Evidence for a precursor of the high-affinity metastasis-associated murine laminin receptor. Biochemistry. 1989; 28(18): 7476-86, 1989.
28. Buto S, Tagliabue E, Ardini E, et al. Formation of the 67-kDa laminin receptor by acylation of the precursor. J Cell Biochem. 1998; 69(3): 244-51.
29. Hundt C, Peyrin J M, Haik S, et al. Identification of interaction domains of the prion protein with its 37-kDa/67-kDa laminin receptor. Embo J. 2001; 20(21): 5876-86.
30. Leucht C, Simoneau S, Rey C, et al. The 37 kDa/67 kDa laminin receptor is required for PrP(Sc) propagation in scrapie-infected neuronal cells. EMBO Rep. 2003; 4(3): 290-5.
31. Gauczynski S, Peyrin J M, Haik S, et al. The 37-kDa/67-kDa laminin receptor acts as the cell-surface receptor for the cellular prion protein. Embo J. 2001; 20(21): 5863-75.
32. Shmakov A N, Bode J, Kilshaw P J, Ghosh S. Diverse patterns of expression of the 67-kD laminin receptor in human small intestinal mucosa: potential binding sites for prion proteins? J Pathol. 2000; 191(3): 318-22.
33. Rieger R, Edenhofer F, Lasmezas C I, Weiss S. The human 37-kDa laminin receptor precursor interacts with the prion protein in eukaryotic cells. Nat Med. 1997; 3(12): 1383-8.
34. Rieger R, Lasmezas C I, Weiss S. Role of the 37 kDa laminin receptor precursor in the life cycle of prions. Transfus Clin Biol. 1999; 6(1): 7-16.
35. Byrnes A P, Griffin D E. Binding of Sindbis virus to cell surface heparan sulfate. J. Virol. 1998; 72(9): 7349-56.
36. Taylor R M, Hurlbut H S. Isolation of coxsackie-like viruses from mosquitoes. J Egypt Med Assoc. 1953; 36: 489-94.
37. Taylor R M, Hurlbut H S, Work T H, Kingsbury J R, Frothingham T E. Sindbis virus: A newly recognized arthropod-transmitted virus. Am J Trop Med Hyg. 1955; 4: 844-46.
38. Stojdl D F, Lichty B D, tenOever B R, et al. VSV strains with defects in their ability to shutdown innate immunity are potent systemic anti-cancer agents. Cancer Cell. 2003; 4(4): 263-75.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for monitoring anti-cancer therapy in a mammal harboring a solid tumor which expresses higher levels of LAMR than normal tissues comprising the steps of
   a) administering to a mammal harboring a solid tumor a diagnostically effective amount of a replication defective Sindbis virus vector comprising a gene encoding a detectable label before or substantially simultaneously with the onset of anti-cancer therapy, and determining the amount of said detectable label in the body of said mammal,
   b) administering a diagnostically effective amount of a replication defective Sindbis virus vector comprising a gene encoding a detectable label after said anti-cancer therapy has been completed, and determining the amount of said detectable label in the body of said mammal;
   comparing the amount of said detectable label in steps a) and b)
   wherein diminution in the amount of said detectable label in step b) compared to the amount of said detectable label in step a), is indicative that the number of live cancer cells that were alive has decreased;
   wherein the amount of said cancer cells is proportional to the amount of label produced by said cancer cells and said label is detected by imaging.

2. The method of claim 1, wherein said gene is selected from Herpes virus thymidine kinase, dopamine-2 receptor, green fluorescent protein, Firefly luciferase and *Renilla* luciferase.

3. The method of claim 1 further comprising administering a means for detecting said label.

4. The method of claim 3 wherein said detectable label is the Herpes virus thymidine kinase gene and said means for detecting said label is radiolabeled 2'-fluoro-2'-deoxy-1-beta-D-arbinofuranosyl-5-iodouracil (FIAU).

5. The method of claim 4 wherein said means is identified by Positron Emission Tomography.

6. The method of claim 3, wherein said label is green fluorescent protein and said label is detected by (a) obtaining a tissue section of said cancer cells and (b) examining said tissue section by fluorescence microscopy.

7. The method of claim 3, wherein said label is Firefly or *Renilla* luciferase and said label is detected by Cooled Charge-Coupled Device cameras.

8. A method for identifying cancer cells that express greater amounts of LAMR than normal tissues in the body of a mammal comprising administering to a mammal harboring a solid tumor a diagnostically effective amount of a replication defective Sindbis virus vector comprising a gene encoding a detectable label, and assaying for said label, wherein said cell is a cancer cell if it expresses said label and wherein said label is identified by imaging.

9. The method of claim 8 wherein said gene encoding said detectable label is selected from Herpes virus thymidine kinase, green fluorescent protein, Firefly luciferase and *Renilla* luciferase.

10. The method of claim 9 wherein said cancer cell is identified before anti-cancer therapy is administered to said mammal.

11. The method of claim 9 wherein said cancer cell is identified after the administration of anti-cancer therapy.

12. The method of claim 9 further comprising administering a means for detecting said label.

* * * * *

UNITED STATES PATENT AND TRADEMARK OFFICE
CERTIFICATE OF CORRECTION

PATENT NO. : 7,910,093 B2
APPLICATION NO. : 10/920030
DATED : March 22, 2011
INVENTOR(S) : Daniel Meruelo and Jen-Chieh Tseng It is certified that error appears in the above-identified patent and that said Letters Patent is hereby corrected as shown below:

In the Specification

Column 1, Lines 7-11 should read:
--STATEMENT REGARDING FEDERALLY SPONSORED RESEARCH OR DEVELOPMENT
This invention was made with government support under grant numbers CA068498 and CA022247 awarded by The National Institutes of Health. The government has certain rights in the invention.--

Signed and Sealed this
Twenty-second Day of November, 2022

Katherine Kelly Vidal
*Director of the United States Patent and Trademark Office*